United States Patent [19]
Ono et al.

[11] Patent Number: 5,877,174
[45] Date of Patent: Mar. 2, 1999

[54] 2,3-DIKETOPIPERAZINE DERIVATIVES OR THEIR SALTS

[75] Inventors: Satoshi Ono; Tetsuo Yamafuji; Hirohiko Yamamoto; Hiroyuki Egawa; Yousuke Furuta; Hidetoshi Kaga, all of Toyama, Japan

[73] Assignee: Toyama Chemical Co., Ltd., Tokyo, Japan

[21] Appl. No.: 849,074

[22] PCT Filed: Nov. 24, 1995

[86] PCT No.: PCT/JP95/02391

§ 371 Date: May 30, 1997

§ 102(e) Date: May 30, 1997

[87] PCT Pub. No.: WO96/16947

PCT Pub. Date: Jun. 6, 1996

[30] Foreign Application Priority Data

Dec. 1, 1994 [JP] Japan ..................................... 6-323813
Dec. 27, 1994 [JP] Japan ..................................... 6-336883
Dec. 27, 1994 [JP] Japan ..................................... 6-336884

[51] Int. Cl.⁶ ..................... A61K 31/495; C07D 401/06; C07D 409/06; C07D 241/08
[52] U.S. Cl. .......................... 514/252; 514/253; 514/255; 544/295; 544/360; 544/368; 544/377; 544/379; 544/385; 544/405; 544/408
[58] Field of Search ..................... 544/408, 295, 544/360, 368, 377, 379, 385; 514/252, 253, 255

[56] References Cited

U.S. PATENT DOCUMENTS 4,948,892 8/1990 Tanabe et al. ........................... 544/385

FOREIGN PATENT DOCUMENTS 2 019 820 11/1971 Germany .
19515500 10/1996 Germany .
WO 96/02503 2/1996 WIPO .

OTHER PUBLICATIONS

Hori et al, *Chem. Pharm. Bull. 29*, pp. 386–389, 1981.

*Primary Examiner*—Emily Bernhardt
*Attorney, Agent, or Firm*—Oblon, Spivak, McClelland, Maier & Neustadt, P.C.

[57] ABSTRACT

The present invention relates to a 2,3-diketopiperazine derivative or a salt thereof, which has inhibitory effect on platelet aggregation because of glycoprotein IIb/IIIa receptor antagonism and hence is useful as a prophylactic and therapeutic agent for diseases associated with platelet aggregation. General formula:

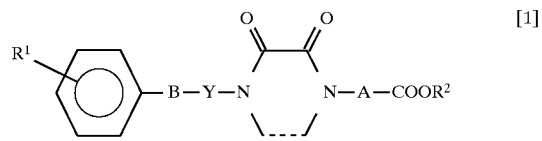

wherein $R^1$ represents a protected or unprotected amidino group; $R^2$ represents a hydrogen atom or a carboxyl-protecting group; A represents a substituted or unsubstituted lower alkylene group; B represents —O—, —CONH—, —NHCO— or —SO$_2$NH—; Y represents a substituted or unsubstituted lower alkylene group; and the broken line represents a single bond or a double bond.

31 Claims, No Drawings

2,3-DIKETOPIPERAZINE DERIVATIVES OR THEIR SALTS

TECHNICAL FIELD

This invention relates to a non-peptide compound having inhibitory effect on platelet aggregation because of glycoprotein IIb/IIIa receptor antagonism.

BACKGROUND ART

Platelet aggregation plays an important role in thrombosis and blood coagulation. When a blood vessel is injured, platelets are activated, for example, by collagen under the vascular endothelium, so that binding of fibrinogen to the platelets, i.e., platelet aggregation is caused, resulting in thrombosis. As the final step in platelet aggregation, there is a step in which glycoprotein IIb/IIIa receptor on the platelet surface is activated and then bonded to fibrinogen. Therefore, an inhibitor capable of preventing the combination of glycoprotein IIb/IIIa receptor and an adhesion protein such as fibrinogen is considered useful for preventing thrombosis and blood coagulation.

It is considered that in the binding of fibrinogen to glycoprotein IIb/IIIa receptor, the amino acid sequence Arg-Gly-Asp-Ser (hereinafter referred to as RGDS) portion on fibrinogen is an active site. Therefore, RGDS analogues have been developed as antagonist for glycoprotein IIb/IIIa receptor. They are expected as agents for suppressing metastasis of cancerous cells.

As such competitors, peptide derivatives containing an amino acid sequence Arg-Gly-Asp are known. They, however, are not sufficient in ease of oral absorption, etc. when used as a pharmaceutical.

DISCLOSURE OF THE INVENTION

In view of such conditions, the present inventors earnestly investigated and consequently found that a novel 2,3-diketopiperazine derivative represented by the general formula [1] or a salt thereof has inhibitory effect on platelet aggregation because of glycoprotein IIb/IIIa receptor antagonism and hence is useful as a prophylactic and therapeutic agent for diseases associated with platelet aggregation, for example, an antithrombotic agent, whereby the present invention has been accomplished. The present invention is explained below in detail.

The present invention relates to a novel 2,3-diketopiperazine derivative represented by the following general formula, or its salt:

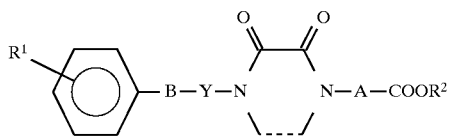

[1]

wherein $R^1$ represents a protected or unprotected amidino group; $R^2$ represents a hydrogen atom or a carboxyl-protecting group; A represents a substituted or unsubstituted lower alkylene group; B represents —O—, —CONH—, —NHCO— or —SO$_2$NH—; Y represents a substituted or unsubstituted lower alkylene group; and the broken line represents a single bond or a double bond.

In the present specification, unless otherwise specified, the term "halogen atom" means a fluorine atom, a chlorine atom, a bromine atom or an iodine atom; the term "lower alkyl group" means a straight chain or branched chain $C_{1-6}$alkyl group such as methyl, ethyl, n-propyl, isopropyl, n-butyl, sec-butyl, tert-butyl, pentyl, hexyl or the like; the term "lower alkylene group" means a straight chain or branched chain $C_{1-6}$alkylene group such as methylene, ethylene, propylene, trimethylene, tetramethylene, pentamethylene, 1-methyltrimethylene, 1-ethyltriethylene, 1-isopropyltriethylene, 1,1-dimethyltrimethylene, 1,2-dimethyltrimethylene or the like; the term "lower alkylenedioxy group" means a $C_{1-6}$alkylenedioxy group such as methylenedioxy, ethylenedioxy or the like; the term "cycloalkyl group" means a $C_{3-8}$cycloalkyl group such as cyclopropyl, cyclobutyl, cyclopentyl, cyclohexyl or the like; the term "aryl group" means, for example, a phenyl, tolyl or naphthyl group; the term "lower alkoxy group" means a lower alkyl —O— group in which the prefix "lower alkyl" means the above-exemplified lower alkyl group; the term "aryloxy group" means an aryl —O— group in which the prefix "aryl" means the above-exemplified aryl group; the term "aralkyl group" means an aryl-lower alkyl group, in which the term "lower alkyl" means the above-exemplified lower alkyl group, such as benzyl, benzhydryl, trityl, phenethyl or the like; and the term "heterocyclic group" means a 5-membered or 6-membered cyclic group containing at least one hetero atom selected from the group consisting of oxygen atom, sulfur atom and nitrogen atom as the hetero atom forming the ring or a fused cyclic group thereof, such as furyl, pyrrolyl, imidazolyl, pyrazolyl, pyrrolidinyl, imidazolydinyl, pirazolidinyl, pyridyl, piperidinyl, pyrazinyl, pyrimidinyl, pyridazinyl, piperazinyl, triazolyl, tetrazolyl, oxazolyl, isoxazolyl, thiazolyl, isothiazolyl, furazanyl, morpholinyl, furanyl, thienyl, pyranyl, thiopyranyl, benzothienyl, benzoxanyl, indolyl, benzothiazolyl, benzimidazolyl, quinolyl, naphthyridinyl, chromanyl or the like.

The lower alkylene group for A may be substituted by at least one member selected from a lower alkyl group, a lower alkoxy group, a cycloalkyl group, an aryl group, an aralkyl group, a heterocyclic group, a carbamoyl group, a protected or unprotected amino group, a protected or unprotected hydroxyl group, and a protected or unprotected carboxyl group.

The above-exemplified substituents of A may be substituted by at least one member selected from a halogen atom, a lower alkyl group, a lower alkoxy group, a protected or unprotected hydroxyl group, a lower alkylenedioxy group and an aralkyl group.

The lower alkylene group for Y may be substituted by at least one member selected from a lower alkyl group, a lower alkoxy group, a cycloalkyl group, an aryl group, an aralkyl group, a heterocyclic group, and a protected or unprotected hydroxyl group.

The above-exemplified substituents of Y may be substituted by at least one member selected from a halogen atom, a lower alkyl group, a lower alkoxy group, a protected or unprotected hydroxyl group, and an aralkyl group.

The carboxyl-protecting group includes all the conventional groups usable as carboxyl-protecting groups, for example, lower alkyl groups such as methyl, ethyl, n-propyl, isopropyl, 1,1-dimethylpropyl, n-butyl, tert-butyl and the like; aryl groups such as phenyl, naphthyl and the like; ar-lower alkyl groups such as benzyl, diphenylmethyl, triphenylmethyl, p-nitrobenzyl, p-methoxybenzyl, bis(p-methoxyphenyl)methyl and the like; acyl-lower alkyl groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-lower alkyl groups such as 2,2,2-trichloroethyl and the like; lower alkylsilylalkyl groups such as 2-(trimethylsilyl)ethyl and the like; acyloxy-lower alkyl groups such as acetoxymethyl, propionyloxymethyl, pivaloyloxymethyl and the like; nitrogen-containing heterocyclic lower alkyl groups such as phthalimido-methyl, succinimidomethyl and the like; cycloalkyl groups such as cyclohexyl and the like; lower alkoxy-lower alkyl groups such as methoxymethyl, methoxyethoxy-methyl, 2-(trimethylsilyl)ethoxymethyl and the like; ar-lower alkoxy-lower alkyl groups such as benzyloxy-methyl and the like; lower alkylthio-lower alkyl groups such as methylthiomethyl, 2-methylthioethyl and the like; arylthio-lower alkyl groups such as phenylthiomethyl and the like; lower alkenyl groups such as 1,1-dimethyl-2-propenyl, 3-methyl-3-butenyl, allyl and the like; and lower alkyl-substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The protecting group for each of the amidino group and the amino group includes all the conventional groups usable as amino-protecting groups, for example, acyl groups such as trichloroethoxycarbonyl, tribromo-ethoxycarbonyl, benzyloxycarbonyl, p-nitrobenzyloxy-carbonyl, o-bromobenzyloxycarbonyl, (mono-, di- or tri-) chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo)benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl and the like; ar-lower alkyl groups such as benzyl, diphenyl-methyl, trityl and the like; arylthio groups such as 2-nitrophenylthio, 2,4-dinitrophenylthio and the like; alkyl- or aryl-sulfonyl groups such as methanesulfonyl, p-toluenesulfonyl and the like; di-lower alkylamino-lower alkylidene groups such as N,N-dimethylamino-methylene and the like; ar-lower alkylidene groups such as benzylidene, 2-hydroxybenzylidene, 2-hydroxy-5-chlorobenzylidene, 2-hydroxy-1-naphthylmethylene and the like; nitrogen-containing heterocyclic alkylidene groups such as 3-hydroxy-4-pyridylmethylene and the like; cycloalkylidene groups such as cyclohexylidene, 2-ethoxycarbonylcyclohexylidene, 2-ethoxycarbonylcyclo-pentylidene, 2-acetylcyclohexylidene, 3,3-dimethyl-5-oxycyclohexylidene and the like; diaryl- or diar-lower alkylphosphoryl groups such as diphenylphosphoryl, dibenzylphosphoryl and the like; oxygen-containing heterocyclic alkyl groups such as 5-methyl-2-oxo-2H-1,3-dioxol-4-yl-methyl and the like; and lower alkyl-substituted silyl groups such as trimethylsilyl and the like.

The protecting group for the hydroxyl group includes all the conventional groups usable as hydroxyl-protecting groups, for example, acyl groups such as benzyloxycarbonyl, 4-nitrobenzyloxycarbonyl, 4-bromo-benzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxy-carbonyl, S-benzylthiocarbonyl, 4-ethoxy-1-naphthyloxy-carbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl and the like; lower alkyl groups such as methyl, tert-butyl, 2,2,2-trichloroethyl, 2-trimethylsilylethyl and the like; lower alkenyl groups such as allyl and the like; ar-lower alkyl groups such as benzyl, p-methoxybenzyl, 3,4-dimethoxybenzyl, diphenylmethyl, trityl and the like; oxygen-containing or sulfur-containing heterocyclic groups such as tetrahydrofuryl, tetrahydropyranyl, tetrahydrothiopyranyl and the like; lower alkoxy- or lower alkylthio-lower alkyl groups such as methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl and the like; alkyl- or aryl-sulfonyl groups such as methanesulfonyl, p-toluenesulfonyl and the like; and lower alkyl-substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The salt of the compound of the general formula [1] includes usually known salts at basic groups such as amino group and the like and salts at acidic groups such as carboxyl group and the like. The salts at the basic groups include, for example, salts with mineral acids such as hydrochloric acid, hydrobromic acid, phosphoric acid, sulfuric acid and the like; salts with organic carboxylic acids such as tartaric acid, formic acid, acetic acid, fumaric acid, maleic acid, citric acid, trichloroacetic acid, trifluoroacetic acid and the like; and salts with sulfonic acids such as methanesulfonic acid, benzenesulfonic acid, p-toluenesulfonic acid, mesitylenesulfonic acid, naphthalenesulfonic acid and the like. The salts at the acidic groups include, for example, salts with alkali metals such as sodium, potassium and the like; salts with alkaline earth metals such as calcium, magnesium and the like; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine, guanidine, hydrazine, quinine, cinchonine and the like.

Of the above-exemplified salts, pharmaceutically acceptable salts are preferable as the salt of the compound of the general formula [1].

When the compound of the general formula [1] or its salt has isomers (for example, optical isomers, geometrical isomers, tautomers and the like), the present invention includes these isomers, and the compound or its salt may be in the form of a solvate or hydrate or in any of various crystal forms.

Of the compounds according to the present invention, preferable are compounds in which B represents —O—; Y represents a lower alkylene group; $R^1$ represents an amidino group; the broken line represents a single bond; and A represents a lower alkylene group which may be substituted by at least one member selected from a substituted or unsubstituted lower alkyl, lower alkoxy, cycloalkyl, aryl, aralkyl, heterocyclic or carbamoyl group, and a protected or unprotected, or substituted or unsubstituted amino, hydroxyl or carboxyl group. Particularly preferable are compounds in which A represents a lower alkylene group substituted by a phenyl or 5-membered or 6-membered heterocyclic group which may be substituted by a halogen atom, a lower alkoxy group or a 1,3-methylenedioxy group.

Typical examples of the compound of the present invention are, for example, the following compounds:

[4-[3-(4-Amidinophenoxy)propyl]-2,3-dioxopiperazin-1-yl] acetic acid,
[4-[4-(4-Amidinophenoxy)butyl]-2,3-dioxopiperazin-1-yl] acetic acid,
3-[4-[3-(4-Amidinophenoxy)propyl]-2,3-dioxopiperazin-1-yl]-3-(pyridin-2-yl)propionic acid,
3-[4-[3-(4-Amidinophenoxy)propyl]-2,3-dioxopiperazin-1-yl]-3-(pyridin-3-yl)propionic acid,
3-[4-[3-(4-Amidinophenoxy)propyl]-2,3-dioxopiperazin-1-yl]-3-(pyridin-4-yl)propionic acid,
3-[4-[4-(4-Amidinophenoxy)butyl]-2,3-dioxopiperazin-1-yl]-3-(pyridin-2-yl)propionic acid,
3-[4-[4-(4-Amidinophenoxy)butyl]-2,3-dioxopiperazin-1-yl]-3-(pyridin-3-yl)propionic acid,
3-[4-[4-(4-Amidinophenoxy)butyl]-2,3-dioxopiperazin-1-yl]-3-(pyridin-4-yl)propionic acid,
3-[4-[3-(4-Amidinophenoxy)propyl]-2,3-dioxopiperazin-1-yl]-3-methylpropionic acid,
3-[4-[3-(4-Amidinophenoxy)propyl]-2,3-dioxopiperazin-1-yl]-3-ethylpropionic acid,
3-[4-[3-(4-Amidinophenoxy)propyl]-2,3-dioxopiperazin-1-yl]-3-(isopropyl)propionic acid,
3-[4-[3-(4-Amidinophenoxy)propyl]-2,3-dioxopiperazin-1-yl]-3-(cyclopropyl)propionic acid,
3-[4-[3-(4-Amidinophenoxy)propyl]-2,3-dioxopiperazin-1-yl]-3-(cyclohexyl)propionic acid,
3-[4-[4-(4-Amidinophenoxy)butyl]-2,3-dioxopiperazin-1-yl]-3-methylpropionic acid,
3-[4-[4-(4-Amidinophenoxy)butyl]-2,3-dioxopiperazin-1-yl]-3-ethylpropionic acid,
3-[4-[4-(4-Amidinophenoxy)butyl]-2,3-dioxopiperazin-1-yl]-3-(isopropyl)propionic acid,
3-[4-[4-(4-Amidinophenoxy)butyl]-2,3-dioxopiperazin-1-yl]-3-(cyclopropyl)propionic acid,
3-[4-[4-(4-Amidinophenoxy)butyl]-2,3-dioxopiperazin-1-yl]-3-(cyclohexyl)propionic acid,
3-[4-[3-(4-Amidinophenoxy)propyl]-2,3-dioxopiperazin-1-yl]-3-phenylpropionic acid,
3-[4-[3-(4-Amidinophenoxy)propyl]-2,3-dioxopiperazin-1-yl]-2-phenylpropionic acid,
3-[4-[4-(4-Amidinophenoxy)butyl]-2,3-dioxopiperazin-1-yl]-3-phenylpropionic acid,
3-[$^4$-[4-(4-Amidinophenoxy)butyl]-2,3-dioxopiperazin-1-yl]-2-phenylpropionic acid,
3-[$^4$-[3-(4-Amidinophenoxy)propyl]-2,3-dioxopiperazin-1-yl]-3-(4-fluorophenyl)propionic acid,
3-[$^4$-[3-($^4$-Amidinophenoxy)propyl]-2,3-dioxopiperazin-1-yl]-3-(3-fluorophenyl)propionic acid,
3-[4-[3-(4-Amidinophenoxy)propyl]-2,3-dioxopiperazin-1-yl]-3-(2-fluorophenyl)propionic acid,
3-[4-[3-(4-Amidinophenoxy)propyl]-2,3-dioxopiperazin-1-yl]-3-(2,4-difluorophenyl)propionic acid,
3-[4-[4-(4-Amidinophenoxy)butyl]-2,3-dioxopiperazin-1-yl]-3-(4-fluorophenyl)propionic acid,
3-[4-[4-(4-Amidinophenoxy)butyl]-2,3-dioxopiperazin-1-yl]-3-(3-fluorophenyl)propionic acid,
3-[4-[4-(4-Amidinophenoxy)butyl]-2,3-dioxopiperazin-1-yl]-3-(2-fluorophenyl)propionic acid,
3-[4-[4-(4-Amidinophenoxy)butyl]-2,3-dioxopiperazin-1-yl]-3-(2,4-difluorophenyl)propionic acid,
3-[4-[3-(4-Amidinophenoxy)propyl]-2,3-dioxopiperazin-1-yl]-3-(4-chlorophenyl)propionic acid,
3-[4-[3-(4-Amidinophenoxy)propyl]-2,3-dioxopiperazin-1-yl]-3-(3-chlorophenyl)propionic acid,
3-[4-[3-(4-Amidinophenoxy)propyl]-2,3-dioxopiperazin-1-yl]-3-(2-chlorophenyl)propionic acid,
3-[4-[3-(4-Amidinophenoxy)propyl]-2,3-dioxopiperazin-1-yl]-3-(2,4-dichlorophenyl)propionic acid,
3-[$^4$-[4-(4-Amidinophenoxy)butyl]-2,3-dioxopiperazin-1-yl]-3-(4-chlorophenyl)propionic acid,
3-[$^4$-[$^4$-(4-Amidinophenoxy)butyl]-2,3-dioxopiperazin-1-yl]-3-(3-chlorophenyl)propionic acid,
3-[$^4$-[$^4$-($^4$-Amidinophenoxy)butyl]-2,3-dioxopiperazin-1-yl]-3-(2-chlorophenyl)propionic acid,
3-[$^4$-[$^4$-($^4$-Amidinophenoxy)butyl]-2,3-dioxopiperazin-1-yl]-3-(2,4-dichlorophenyl)propionic acid,
3-[4-[3-(4-Amidinophenoxy)propyl]-2,3-dioxopiperazin-1-yl]-3-(4-methoxyphenyl)propionic acid,
3-[4-[3-(4-Amidinophenoxy)propyl]-2,3-dioxopiperazin-1-yl]-3-(3-methoxyphenyl)propionic acid,
3-[4-[3-(4-Amidinophenoxy)propyl]-2,3-dioxopiperazin-1-yl]-3-(2-methoxyphenyl)propionic acid,
3-[4-[3-(4-Amidinophenoxy)propyl]-2,3-dioxopiperazin-1-yl]-3-(2-thienyl)propionic acid,
3-[4-[3-(4-Amidinophenoxy)propyl]-2,3-dioxopiperazin-1-yl]-3-(3-thienyl)propionic acid,
3-[4-[4-(4-Amidinophenoxy)butyl]-2,3-dioxopiperazin-1-yl]-3-(2-thienyl)propionic acid,
3-[4-[4-(4-Amidinophenoxy)butyl]-2,3-dioxopiperazin-1-yl]-3-(3-thienyl)propionic acid,
3-[4-[3-(4-Amidinophenoxy)propyl]-2,3-dioxopiperazin-1-yl]-3-(2-furyl)propionic acid,
3-[4-[3-(4-Amidinophenoxy)propyl]-2,3-dioxopiperazin-1-yl]-3-(3-furyl)propionic acid,
3-[4-[4-(4-Amidinophenoxy)butyl]-2,3-dioxopiperazin-1-yl]-3-(2-furyl)propionic acid,
3-[4-[4-(4-Amidinophenoxy)butyl]-2,3-dioxopiperazin-1-yl]-3-(3-furyl)propionic acid,
3-[4-[3-(4-Amidinophenoxy)propyl]-2,3-dioxopiperazin-1-yl]-3-(1,3-benzodioxol-5-yl)propionic acid,
3-[4-[4-(4-Amidinophenoxy)butyl]-2,3-dioxopiperazin-1-yl]-3-(1,3-benzodioxol-5-yl)propionic acid,
3-[$^4$-[3-($^4$-Amidinophenoxy)propyl]-2,3-dioxopiperazin-1-yl]-2-[(1,3-benzodioxol-5-yl)methyl]-propionic acid,
3-[4-[4-(4-Amidinophenoxy)butyl]-2,3-dioxopiperazin-1-yl]-2-[(1,3-benzodioxol-5-yl)methyl]propionic acid,
3-[4-[3-(4-Amidinophenoxy)propyl]-2,3-dioxopiperazin-1-yl]-3-(thiazol-2-yl)propionic acid,
3-[4-[3-(4-Amidinophenoxy)propyl]-2,3-dioxopiperazin-1-yl]-3-(thiazol-4-yl)propionic acid,
3-[4-[3-(4-Amidinophenoxy)propyl]-2,3-dioxopiperazin-1-yl]-3-(thiazol-5-yl)propionic acid,
3-[4-[4-(4-Amidinophenoxy)butyl]-2,3-dioxopiperazin-1-yl]-3-(thiazol-2-yl)propionic acid,
3-[4-[4-(4-Amidinophenoxy)butyl]-2,3-dioxopiperazin-1-yl]-3-(thiazol-4-yl)propionic acid,
3-[4-[4-(4-Amidinophenoxy)butyl]-2,3-dioxopiperazin-1-yl]-3-(thiazol-5-yl)propionic acid,
3-[4-[3-(4-Amidinophenoxy)propyl]-2,3-dioxopiperazin-1-yl]-3-[(N-benzyl-N-methyl)carbamoyl]-propionic acid,
3-[4-[4-(4-Amidinophenoxy)butyl]-2,3-dioxopiperazin-1-yl]-3-[(N-benzyl-N-methyl)carbamoyl]-propionic acid,
2-[4-[3-(4-Amidinophenoxy)propyl]-2,3-dioxopiperazin-1-yl]succinic acid,
2-[4-[4-(4-Amidinophenoxy)butyl]-2,3-dioxopiperazin-1-yl]succinic acid,
3-[4-[4-(4-Amidinophenoxy)propyl]-1,2,3,4-tetrahydro-2,3-dioxopyrazin-1-yl]-3-(pyridin -3-yl)-propionic acid,
3-[4-[4-(4-Amidinophenoxy)butyl]-1,2,3,4-tetrahydro- 2,3-dioxopyrazin-1-yl1-3-(pyridin-3-yl)-propionic acid,
3-[4-[3-(4-Amidinophenoxy)propyl]-2,3-dioxopiperazin-1-yl]-3-(1-naphthyl)propionic acid,
3-[4-[3-(4-Amidinophenoxy)propyl]-2,3-dioxopiperazin-1-yl]-3-(2-naphthyl)propionic acid, 3-[4-[3-(4-Amidinophenoxy)propyl]-2,3-dioxopiperazin-1-yl]-3-(benzo[b]thiophen-2-yl)propionic acid,
3-[4-[3-(4-Amidinophenoxy)propyl]-2,3-dioxopiperazin-1-yl]-3-(benzo[b]thiophen-3-yl)propionic acid,
3-[4-[3-(4-Amidinophenoxy)propyl]-2,3-dioxopiperazin-1-yl]-3-(benzo[b]thiophen-5-yl)propionic acid,
3-[4-[3-(4-Amidinophenoxy)propyl]-2,3-dioxopiperazin-1-yl]-3-(benzofuran-2-yl)propionic acid,
3-[4-[3-(4-Amidinophenoxy)propyl]-2,3-dioxopiperazin-1-yl]-3-(benzofuran-3-yl)propionic acid,
3-[4-[3-(4-Amidinophenoxy)propyl]-2,3-dioxopiperazin-1-yl]-3-(benzofuran-5-yl)propionic acid,
3-[4-[2-(4-Amidinophenoxy)ethyl]-2,3-dioxopiperazin-1-yl]-3-(pyridin-3-yl)propionic acid,
3-[4-[3-(4-Amidinophenoxy)propyl]-2,3-dioxopiperazin-1-yl ]-3-(butyl)propionic acid,
3-[4-[2-(4-Amidinobenzoylamino)ethyl]-2,3-dioxopiperazin-1-yl]-3-(pyridin-3-yl)propionic acid,
3-[4-[3-(4-Amidinobenzoylamino)propyl]-2,3-dioxopiperazin-1-yl]-3-(pyridin-3-yl)propionic acid,
[4-[2-(4-Amidinobenzoylamino)ethyl]-2,3-dioxopiperazin-1-yl]acetic acid,
[4-[3-(4-Amidinobenzoylamino)propyl )-2,3-dioxopiperazin-1-yl]acetic acid,
3-[4-[2-(4-Amidinobenzoylamino)ethyl]-2,3-dioxopiperazin-1-yl]-3-(pyridin-2-yl)propionic acid,
3-[4-[2-(4-Amidinobenzoylamino)ethyl)-2,3-dioxopiperazin-1-yl]-3-(pyridin-4-yl)propionic acid,
3-[4-[2-(4-Amidinobenzoylamino)ethyl]-2,3-dioxopiperazin-1-yl]-3-phenylpropionic acid,
3-[4-[2-(4-Amidinobenzoylamino)ethyl]-2,3-dioxopiperazin-1-yl]-2-phenylpropionic acid,
3-[4-[2-(4-Amidinobenzoylamino)ethyl]-2,3-dioxopiperazin-1-yl]-3-(1,3-benzodioxol-5-yl)propionic acid,
3-[4-[2-(4-Amidinobenzoylamino)ethyl]-2,3-dioxopiperazin-1-yl]-2-(1,3-benzodioxol-5-yl)propionic acid,
3-[4-[2-(4-Amidinobenzoylamino)ethyl]-2,3-dioxopiperazin-1-yl]-2-[(1,3-benzodioxol-5-yl)methyl]propionic acid,
3-[4-[2-(4-Amidinobenzoylamino)ethyl]-2,3-dioxopiperazin-1-yl]-3-(thiophen-2-yl)propionic acid,
3-[4-[2-(4-Amidinobenzoylamino)ethyl]-2,3-dioxopiperazin-1-yl]-3-(thiophen-3-yl)propionic acid,
3-[4-[2-(4-Amidinobenzoylamino)ethyl]-2,3-dioxopiperazin-1-yl]-3-methylpropionic acid,
3-[4-[2-(4-Amidinobenzoylamino)ethyl]-2,3-dioxopiperazin-1-yl ]-3-(cyclopropyl)propionic acid,
3-[4-[2-(4-Amidinobenzoylamino)ethyl]-2,3-dioxopiperazin-1-yl]-3-(3-furyl)propionic acid,
3-[4-[2-(4-Amidinobenzoylamino)ethyl]-2,3-dioxopiperazin-1-yl]-3-(2-furyl)propionic acid,
3-[4-[2-(4-Amidinobenzoylamino)ethyl]-2,3-dioxopiperazin-1-yl]-3-(4-fluorophenyl)propionic acid,
3-[4-[2-(4-Amidinobenzoylamino)ethyl)-2,3-dioxopiperazin-1-yl]-3-(4-methoxyphenyl)propionic acid,
3-[4-[2-(4-Amidinobenzoylamino)ethyl]-2,3-dioxopiperazin-1-yl]-3-(4-methylphenyl)propionic acid,
3-[4-[2-(4-Amidinobenzoylamino)ethyl]-2,3-dioxopiperazin-1-yl]-3-(4-aminophenyl)propionic acid,
3-[4-[2-(4-Amidinobenzoylamino)ethyl]-2,3-dioxopiperazin-1-yl]-3-(2,4-difluorophenyl)propionic acid,
3-[4-[2-(4-Amidinobenzoylamino)ethyl]-2,3-dioxopiperazin-1-yl]-3-(N-benzylcarbamoyl)propionic acid,
3-[4-(3-(4-Amidinobenzoylamino)propyl]-2,3-dioxopiperazin-1-yl]-3-(pyridin-2-yl)propionic acid,
3-[4-[3-(4-Amidinobenzoylamino)propyl]-2,3-dioxopiperazin-1-yl ]-3-(pyridin-4-yl)propionic acid,
3-[4-[3-(4-Amidinobenzoylamino)propyl]-2,3-dioxopiperazin-1-yl ]-3-phenylpropionic acid,
3-[4-[3-(4-Amidinobenzoylamino)propyl]-2,3-dioxopiperazin-1-yl]-4-phenylpropionic acid,
3-[4-[3-(4-Amidinobenzoylamino)propyl]-2,3-dioxopiperazin-1-yl]-3-(1,3-benzodioxol-5-yl)propionic acid,
3-[4-[3-(4-Amidinobenzoylamino)propyl]-2,3-dioxopiperazin-1-yl]-2-(1,3-benzodioxol-5-yl)propionic acid,
3-[4-[3-(4-Amidinobenzoylamino)propyl]-2,3-dioxopiperazin-1-yl]-2-[(1,3-benzodioxol-5-yl)methyl]propionic acid,
3-[4-[3-(4-Amidinobenzoylamino)propyl]-2,3-dioxopiperazin-1-yl]-3-(thiophen-2-yl)propionic acid,
3-[4-[3-(4-Amidinobenzoylamino)propyl]-2,3-dioxopiperazin-1-yl]-3-(thiophen-3-yl)propionic acid,
3-[4-[3-(4-Amidinobenzoylamino)propyl]-2,3-dioxopiperazin-1-yl)-3-methylpropionic acid,
3-[4-[3-(4-Amidinobenzoylamino)propyl]-2,3-dioxopiperazin-1-yl]-3-(cyclopropyl)propionic acid,
3-[4-[3-(4-Amidinobenzoylamino)propyl]-2,3-dioxopiperazin-1-yl]-3-(3-furyl)propionic acid,
3-[4-[3-(4-Amidinobenzoylamino)propyl]-2,3-dioxopiperazin-1-yl]-3-(2-furyl)propionic acid,
3-[4-[3-(4-Amidinobenzoylamino)propyl]-2,3-dioxopiperazin-1-yl]-3-(4-fluorophenyl)propionic acid,
3-[4-[3-(4-Amidinobenzoylamino)propyl]-2,3-dioxopiperazin-1-yl]-3-(4-methoxyphenyl)propionic acid,
3-[4-[3-(4-Amidinobenzoylamino)propyl]-2,3-dioxopiperazin-1-yl ]-3-(4-methylphenyl)propionic acid,
3-[4-[3-(4-Amidinobenzoylamino)propyl]-2,3-dioxopiperazin-1-yl]-3-(4-aminophenyl)propionic acid,
3-[4-[3-(4-Amidinobenzoylamino)propyl]-2,3-dioxopiperazin-1-yl]-3-(2,4-difluorophenyl)propionic acid,
3-[4-[3-(4-Amidinobenzoylamino)propyl]-2,3-dioxopiperazin-1-yl]-3-(N-benzylcarbamoyl)propionic acid,
[4-[4-(4-Amidinophenylamino)-4-oxobutyl]-2,3-dioxopiperazin-1-yl]acetic acid,
(4-[3-(4-Amidinobenzenesulfonylamino)propyl]-2,3-dioxopiperazin-1-yl]acetic acid,
[4-[2-(4-Amidinobenzenesulfonylamino)ethyl]-2,3-dioxopiperazin-1-yl]acetic acid,
3-[4-[3-(4-Amidinobenzenesulfonylamino)propyl]-2,3-dioxopiperazin-1-yl]propionic acid,
3-[4-[2-(4-Amidinobenzenesulfonylamino)ethyl]-2,3-dioxopiperazin-1-yl]-3-(pyridin-3-yl)propionic acid,
3-[4-[3-(4-Amidinobenzenesulfonylamino)propyl]-2,3-dioxopiperazin-1-yl ]-3-(pyridin-3-yl)propionic acid,
3-[4-[3-(4-Amidinobenzenesulfonylamino)propyl]-2,3-dioxopiperazin-1-yl]-2-[(1,3-benzodioxol-5-yl)methyl]propionic acid,
[4-[4-(4-Amidinophenylamino)-4-oxobutyl]-2,3-dioxopiperazin-1-yl]acetic acid,
[4-[3-(4-Amidinophenylamino)-3-oxopropyl]-2,3-dioxopiperazin-1-yl]acetic acid,
3-[4-[4-(4-Amidinophenylamino)-4-oxobutyl]-2,3-dioxopiperazin-1-yl]propionic acid,
3-[4-[3-(4-Amidinophenylamino)-3-oxopropyl]-2,3-dioxopiperazin-1-yl]propionic acid, 3-[4-[4-(4-Amidinophenylamino)-4-oxobutyl]-2,3-dioxopiperazin-1-yl]-3-(pyridin-3-yl)propionic acid, 3-[4-[3-(4-Amidinophenylamino)-3-oxopropyl]-2,3-dioxopiperazin-1-yl]-3-(pyridin-3-yl)propionic acid, 3-[4-[4-(4-Amidinophenylamino)-4-oxobutyl]-2,3-dioxopiperazin-1-yl]-3-[(1,3-benzodioxol-5-yl)methyl]-propionic acid, 3-[4-[3-(4-Amidinophenoxy)propyl]-2,3-dioxopiperazin-1-yl]-3-(3-fluorophenyl)propionic acid, 3-[4-[3-(4-Amidinophenoxy)propyl]-2,3-dioxopiperazin-1-yl]-3-(thiophen-3-yl)propionic acid, 3-[4-[3-(4-Amidinophenoxy)propyl]-2,3-dioxopiperazin-1-yl]-3-(2-methylpyridin-3-yl)propionic acid, 3-[4-[3-(4-Amidinophenoxy)propyl]-2,3-dioxopiperazin-1-yl]-3-(3-methylsulfinylphenyl)propionic acid, 3-[4-[3-(4-Amidinophenoxy)propyl]-2,3-dioxopiperazin-1-yl]-3-(2-fluorophenyl)propionic acid, 3-[4-[3-(4-Amidinophenoxy)propyl]-2,3-dioxopiperazin-1-yl]-3-(2-methylphenyl)propionic acid, 3-[4-[3-(4-Amidinophenoxy)propyl]-2,3-dioxopiperazin-1-yl]-3-(3-methylphenyl)propionic acid, 3-(4-[3-(4-Amidinophenoxy)propyl]-2,3-dioxopiperazin-1-yl ]-3-(3-methoxyphenyl)propionic acid, and 3-[4-[3-(4-Amidinophenoxy)propyl]-2,3-dioxopiperazin-1-yl]-3-(pyrimidin-5-yl)propionic acid,

INDUSTRIAL PRODUCTION PROCESS

Processes for producing the compound of the present invention are explained below.

The compound of the present invention can be synthesized according to, for example, the following production processes.

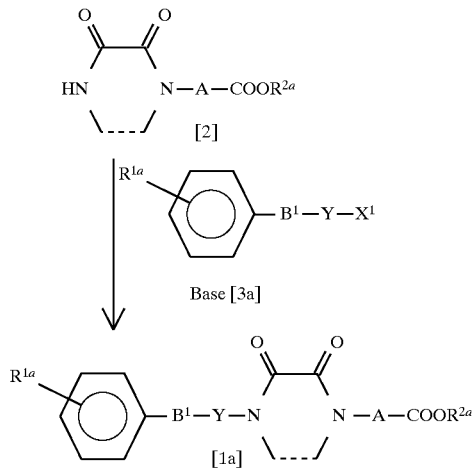

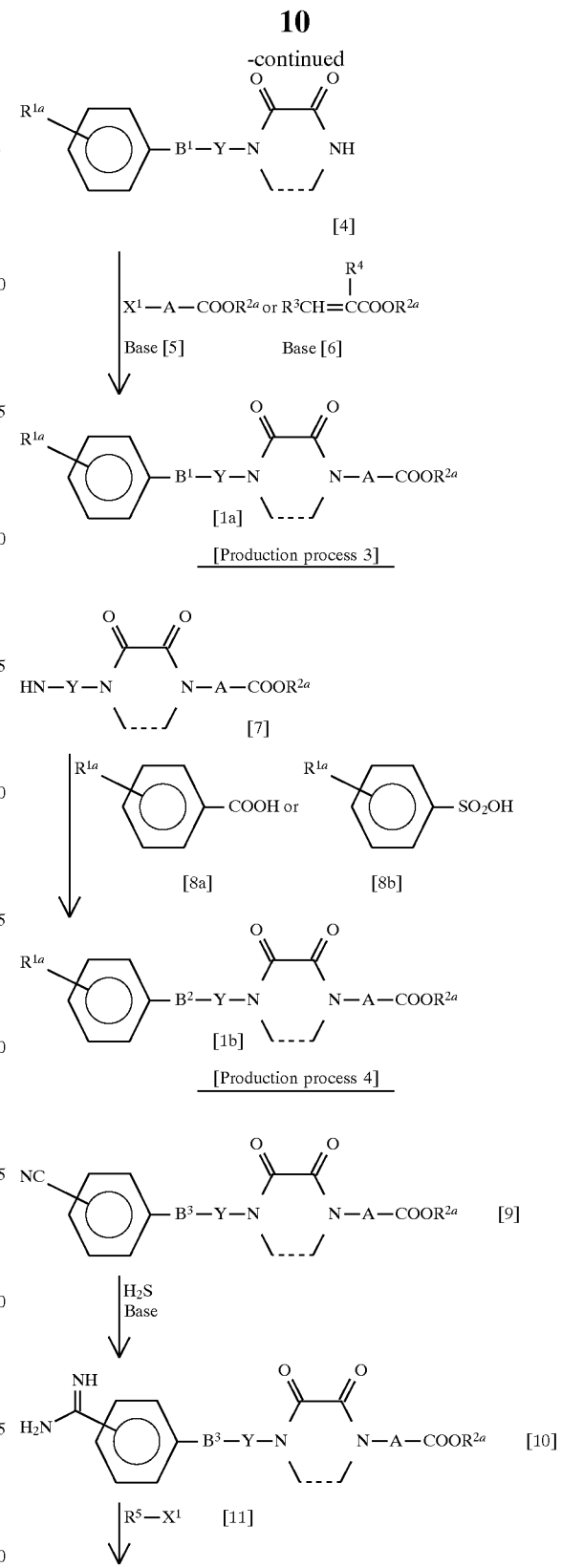

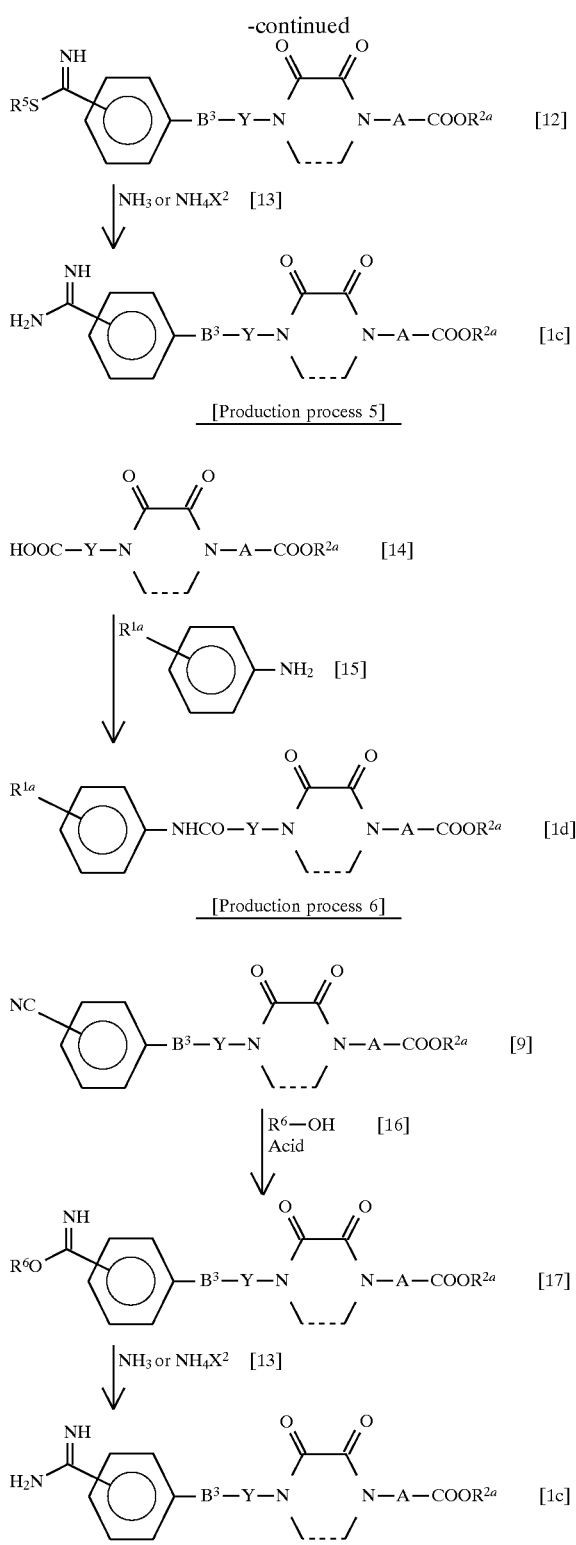

wherein $R^{1a}$ represents a protected amidino group; $R^{2a}$ represents a carboxyl-protecting group; $R^3$ represents a hydrogen atom, a substituted or unsubstituted lower alkyl, cycloalkyl, aryl, aralkyl, heterocyclic or carbamoyl group, or a protected or unprotected carboxyl group; $R^4$ represents a hydrogen atom, a substituted or unsubstituted lower alkyl, cycloalkyl, aryl, aralkyl, heterocyclic or carbamoyl group, a substituted or unsubstituted, or protected or unprotected amino group, or a protected or unprotected carboxyl group; $R^5$ represents a lower alkyl group; $R^6$ represents a lower alkyl group; $X^1$ represents a removing group; $X^2$ represents a halogen atom or an acyloxy group; $B^1$ represents —O—; $B^2$ represents —CONH— or —SO$_2$NH—; $B^3$ represents —O—, —CONH— or —SO$_2$NH—; and A and Y are as defined above.

The removing group includes halogen atoms, methanesulfonyl group, p-toluenesulfonyl group, etc.

[Production process 1]

A compound of the general formula [1a] can be produced by reacting a compound of the general formula [2] with a compound of the general formula [3a] in the presence of a base.

Any solvent may be used in this reaction so long as it has no undesirable influence on the reaction. The solvent includes, for example, aromatic hydrocarbons such as benzene, toluene, xylene and the like; ethers such as dioxane, tetrahydrofuran, anisole, diethylene glycol diethyl ether, dimethyl Cellosolve and the like; nitriles such as acetonitrile and the like; amides such as N,N-dimethylformamide, N,N-dimethylacetamide and the like; halogenated hydrocarbons such as methylene chloride, chloroform, 1,2-dichloroethane and the like; and sulfoxides such as dimethyl sulfoxide and the like. These solvents may be used singly or as a mixture thereof. The base used in the reaction includes, for example, inorganic or organic bases such as sodium hydride, metallic sodium, potassium tert-butoxide, sodium carbonate, potassium carbonate, sodium hydroxide, potassium hydroxide, 1,8-diazabicyclo[5.4.0]undec-7-ene (DBU) and the like.

In the reaction, the compound of the general formula [3a] can be used in an amount of 1 to 50 moles, preferably 1 to 3 moles, per mole of the compound of the general formula [2]. The base can be used in an amount of 0.01 to 50 moles, preferably 1 to 3 moles, per mole of the compound of the general formula [2]. Usually, the reaction can be carried out at –20° C. to +150° C., preferably +10° C. to +100° C. for 1 minute to 24 hours.

[Production process 2]

A compound of the general formula [1a] can be produced by reacting a compound of the general formula [4] with a compound of the general formula [5] or a compound of the general formula [6] in the presence of a base.

Any solvent may be used in this reaction so long as it has no undesirable influence on the reaction. The solvent includes, for example, aromatic hydrocarbons such as benzene, toluene, xylene and the like; alcohols such as methanol, ethanol, propanol and the like; esters such as ethyl acetate and the like; ethers such as dioxane, tetrahydrofuran, anisole, diethylene glycol diethyl ether, dimethyl Cellosolve and the like; nitriles such as acetonitrile and the like; amides such as N,N-dimethylformamide, N,N-dimethylacetamide and the like; halogenated hydrocarbons such as methylene chloride, chloroform, 1,2-dichloroethane and the like; and sulfoxides such as dimethyl sulfoxide and the like. These solvents may be used singly or as a mixture thereof.

The base includes, for example, inorganic or organic bases such as sodium hydride, metallic sodium, potassium tert-butoxide, sodium carbonate, potassium carbonate, sodium hydroxide, potassium hydroxide, 1,8-diazabicyclo[5.4.0]undec-7-ene (DBU) and the like.

In the reaction, the compound of the general formula [5] can be used in an amount of 1 to 50 moles, preferably 1 to 3 moles, per mole of the compound of the general formula [4]. The compound of the general formula [6] can be used in an amount of 1 to 200 moles, preferably 1 to 50 moles, per mole of the compound of the general formula [4].

The base can be used in an amount of 0.01 to 50 moles, preferably 0.1 to 3 moles, per mole of the compound of the general formula [4].

Usually, the reaction can be carried out at −20° C. to +150° C., preferably +10° C. to +100° C. for 1 minute to 24 hours.

[Production process 3]

A compound of the general formula [1b] can be produced by reacting a compound of the general formula [7] or its reactive derivative substituted at the amino group with a compound of the general formula [8a] reactive derivative substituted at the carboxyl group or with a reactive derivative substituted at the sulfo group of the compound of the general formula [8b].

The reactive derivative of the compound of the general formula [8a] includes acid halides, acid anhydrides, activated amides, activated esters, etc. Preferable examples of the reactive derivative are acid chlorides; acid azides; mixed acid anhydrides with acids (e.g. dialkylphosphoric acids such as dimethylphosphoric acid, diethylphosphoric acid and the like; diphenylphosphoric acid; phosphoric halides such as phosphorus oxychloride, phosphorus pentachloride and the like; dialkylphosphonic acids such as dimethylphosphonic acid, diethylphosphonic acid and the like; sulfonic acids such as sulfurous acid, thiosulfuric acid, sulfuric acid, methanesulfonic acid and the like; and aliphatic carboxylic acids such as acetic acid, propionic acid, pivalic acid, trichloroacetic acid and the like, and aromatic carboxylic acids such as benzoic acid and the like); symmetric acid anhydrides; activated amides with imidazole, dimethylpyrazole, triazole, tetrazole, 1-hydroxy-1H-benzotriazole; activated esters such as cyanomethyl ester, methoxymethyl ester, vinyl ester, propargyl ester, p-nitrophenyl ester, 2,4-dinitrophenyl ester, trichlorophenyl ester, pentachlorophenyl ester phenyl thioester, p-nitrophenyl ester, pyranyl ester, pyridyl ester, 8-quinolyl thioester and the like; and esters with N-hydroxy compounds such as N,N-dimethylhydroxylamine, N-hydroxysuccinimide, N-hydroxy-1H-benzatriazole and the like.

The reactive derivative of the compound of the general formula [8b] includes acid chlorides, acid anhydrides, etc.

The reactive derivative of the compound of the general formula [8a] or [8b] may be optionally selected from the above-exemplified derivatives, depending on the kind of the compound of the general formula [8a] or [8b], respectively, to be used.

Preferable examples of the reactive derivative of the compound of the general formula [7] substituted at the amino group are Schiff base type imino compounds or their enamine type tautomers, which are produced by the reaction of the compound of the general formula [7] with a carbonyl compound such as an aldehyde, ketone or the like; silyl derivatives produced by the reaction of the compound of the general formula [7] with a silyl compound such as bis (trimethylsilyl)acetamide, mono(trimethylsilyl)acetamide, bis(trimethylsilyl)urea or the like; and derivatives produced by the reaction of the compound of the general formula [7] with phosphorus trichloride or phosgene.

Any solvent may be used in this reaction so long as it has no undesirable influence on the reaction. The solvent includes, for example, water; ketones such as acetone and the like; alcohols such as methanol, ethanol and the like; aromatic hydrocarbons such as benzene, toluene, xylene and the like; ethers such as dioxane, tetrahydrofuran, anisole, diethylene glycol diethyl ether, dimethyl Cellosolve and the like; nitriles such as acetonitrile and the like; amides such as N,N-dimethylformamide, N,N-dimethylacetamide and the like; halogenated hydrocarbons such as methylene chloride, chloroform, 1,2-dichloroethane and the like; esters such as ethyl acetate and the like; and hetero aromatic compounds such as pyridine and the like. These solvents may be used singly or as a mixture thereof.

When the compound of the general formula [8a] is used in the form of a free acid, the reaction is preferably carried out in the presence of a conventional condensing agent such as N,N'-dicyclohexylcarbodiimide; N-cyclohexyl-N'-morpholinylethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; a 1-alkoxy-1-chloroethyl; a trialkylphosphonic acid; polyphosphoric acid ethyl ester; polyphosphoric acid isopropyl ester; phosphorus oxychloride; phosphorus trichloride; thionyl chloride; oxalyl chloride; a halogenated formic acid alkyl ester such as ethyl chloroformate, isopropyl chloroformate or the like; triphenylphosphine; 2-ethyl-7-hydroxybenzisoxazolium salt; 2-ethyl-5-(m-sulfophenyl)isoxazolium hydroxide internal salt; 1-(p-chlorobenzenesulfonyloxy)-6-chloro-1H-benzotriazole; or the so-called Vilsmeier reagent prepared by reacting N,N-dimethylformamide with thionyl chloride, phosgene, trichloromethyl chloroformate, phosphorus oxychloride, methanesulfonyl chloride or the like.

The reaction may be carried out in the presence of an inorganic or organic base such as sodium hydroxide, potassium hydroxide, sodium carbonate, potassium carbonate, sodium hydrogencarbonate, potassium hydrogencarbonate, triethylamine, N-methylmorpholine, diisopropylethylamine, 1,8-diazabicyclo[5.4.0]undec-7-ene (DBU) or the like.

The compound of the general formula [8a] or [8b] can be used in an amount of 1 to 20 moles, preferably 1 to 3 moles, per mole of the compound of the general formula [7]. Usually, the reaction can be carried out at −50° C. to +150° C., preferably −30° C. to +100° C. for 1 minute to 24 hours.

[Production process 4]

(1) A compound of the general formula [10] can be produced by reacting a compound of the general formula [9] with hydrogen sulfide in the presence of a base.

The base used in this reaction includes, for example, ammonia, triethylamine and diethylisopropylamine.

Any solvent may be used in this reaction so long as it has no undesirable influence on the reaction. The solvent includes, for example, alcohols such as methanol, ethanol and the like; ethers such as tetrahydrofuran, dioxane and the like; and hetero aromatic compounds such as pyridine and the like. These solvents may be used singly or as a mixture thereof.

Each of hydrogen sulfide and the base can be used in an amount of 1 to 500 moles, preferably 1 to 100 moles, respectively, per mole of the compound of the general formula [9] or its salt.

Usually, the reaction can be carried out at 0° C. to +150° C., preferably +10° C. to +100° C. for 1 minute to 24 hours.

(2) A compound of the general formula [12] can be produced by reacting the compound of the general formula [10] with a compound of the general formula [11].

Any solvent may be used in this reaction so long as it has no undesirable influence on the reaction.

The solvent includes, for example, ketones such as acetone and the like; alcohols such as methanol, ethanol and the like; ethers such as dioxane, tetrahydrofuran, anisole, diethylene glycol diethyl ether, dimethyl Cellosolve and the like; dimethyl sulfoxide; amides such as N,N-dimethylformamide, N,N-dimethylacetamide and the like; and esters such as ethyl acetate and the like. These solvents may be used singly or as a mixture thereof.

The compound of the general formula [11] can be used in an amount of 1 to 100 moles, preferably 1 to 10 moles, per mole of the compound of the general formula [10] or its salt.

Usually, the reaction can be carried out at −10° C. to +150° C., preferably +20° C. to +120° C. for 1 minute to 24 hours.

The compound of the general formula [12] can be used in the subsequent reaction without isolation.

(3) A compound of the general formula [1c] can be produced by reacting the compound of the general formula [12] with ammonia or a compound of the general formula [13].

Any solvent may be used in this reaction so long as it has no undesirable influence on the reaction. The solvent includes, for example, ketones such as acetone and the like; alcohols such as methanol, ethanol and the like; ethers such as dioxane, tetrahydrofuran, anisole, diethylene glycol diethyl ether, dimethyl Cellosolve and the like; amides such as N,N-dimethylformamide, N,N-dimethylacetamide and the like; and dimethyl sulfoxide. These solvents may be used singly or as a mixture thereof.

The compound of the general formula [13] includes ammonium salts such as ammonium chloride, ammonium bromide, ammonium acetate and the like.

Ammonia or the compound of the general formula [13] can be used in an amount of 1 to 100 moles, preferably 1 to 10 moles, per mole of the compound of the general formula [12] or its salt.

Usually, the reaction can be carried out at 0° C. to +150° C., preferably +20° C. to +120° C. for 1 minute to 24 hours.

[Production process 5]

A compound of the general formula [1d] can be produced by reacting a compound of the general formula [14], its reactive derivative substituted at the carboxyl group, or a salt of the compound of the general formula [14] or the derivative thereof with a compound of the general formula [15], its reactive derivative substituted at the amino group, or a salt of the compound of the general formula [15] or the derivative thereof.

Examples of the reactive derivative of the compound of the general formula [14] substituted at the carboxyl group and the reactive derivative of the compound of the general formula [15] substituted at the amino group are the same reactive derivatives substituted at the carboxyl group or the amino group, respectively, as those exemplified in production process 3.

Examples of the solvent, condensing agent and base which are used in this reaction are the same as those given in production process 3.

The compound of the general formula [15] can be used in an amount of 1 to 20 moles, preferably 1 to 3 moles, per mole of the compound of the general formula [14]. Usually, the reaction can be carried out at −50° C. to +150° C., preferably −30° C. to +100° C. for 1 minute to 24 hours.

[Production process 6]

(1) A compound of the general formula [17] can be produced by reacting a compound of the general formula [9] with a compound of the general formula [16] in the presence of an acid.

In this reaction, the compound of the general formula [16] may be used also as a solvent, or any other solvent may be used so long as it has no undesirable influence on the reaction. This solvent includes, for example, esters such as ethyl acetate and the like; ethers such as dioxane, tetrahydrofuran, anisole, diethylene glycol diethyl ether and the like; and halogenated hydrocarbons such as methylene chloride, chloroform, 1,2-dichloroethane and the like. These solvents may be used singly or as a mixture thereof.

The acid includes hydrogen chloride, hydrobromic acid, perchloric acid, p-toluenesulfonic acid, methanesulfonic acid, etc.

In the reaction, the compound of the general formula [16] can be used in an amount of 1 to 1,000 moles, preferably 10 to 100 moles, per mole of the compound of the general formula [9].

The acid can be used in an amount of 1 to 200 moles, preferably 5 to 100 moles, per mole of the compound of the general formula [9].

Usually, the reaction can be carried out at −30° C. to +150° C., preferably +10° C. to +50° C. for 30 minutes to 24 hours.

(2) A compound of the general formula [1c] can be produced by reacting the compound of the general formula [17] with ammonia or a compound of the general formula [13].

Examples of the base, the solvent and the compound of the general formula [13] which are used in this reaction are the same bases, solvents and compounds of the general formula [13] as those exemplified in production process 4 (3).

Usually, the reaction can be carried out at 0° to +150° C., preferably +20° C. to +120° C. for 1 minute to 24 hours.

In the production processes explained above, the compounds of the general formulas [2], [3a], [4], [5], [6], [7], [8a], [8b], [9], [10], [12], [14] and [15] and the reactive derivatives of the compounds of the general formulas [7], [8a], [8b], [14] and [15] may be used in the form of a salt. Examples of the salt are the same salts as those exemplified as the salt of the compound of the general formula [1].

The compounds of the general formula [1a], [1b], [1c] and [1d] can be converted to their respective salts. Examples of the salts are the same salts as those exemplified as the salt of the compound of the general formula [1].

Usually, each of the thus obtained compounds of the general formulas [1a], [1b], [1c] and [1d] or their salts can be converted to the compound of the general formula [1] or its salt by a well-known elimination reaction.

In addition, the compound of the general formula [1] or its salt can be converted to another compound of the general formula [1] or its salt by subjecting the compound of the general formula [1] or salt thereof to one or a proper combination of per se well-known reactions such as oxidation, reduction, rearrangement, substitution, halogenation, dehydration, hydrolysis and the like.

Next processes for producing the compounds of the general formulas [2], [3a], [4], [7], [9] and [14], which are starting materials for producing the compound of the present invention are explained below.

The compounds of the general formulas [2], [3a], [4], [7], [9] and [14] can be synthesized, for example, by the following production processes.

[Production process A]
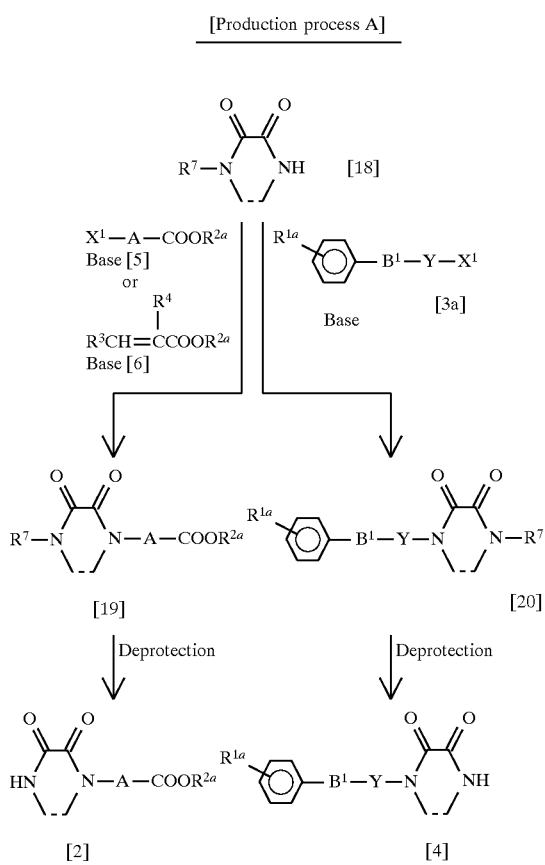
[Production process B]
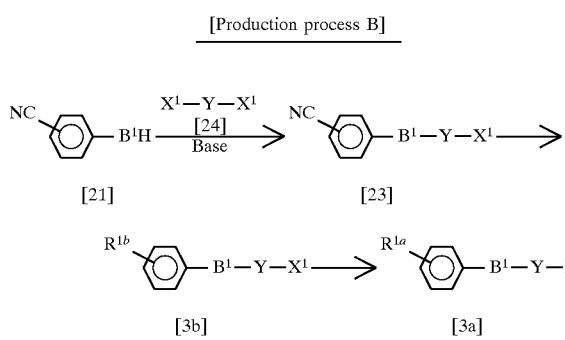
[Production process C]
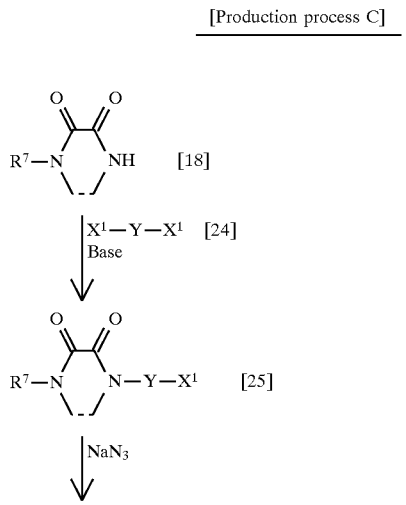
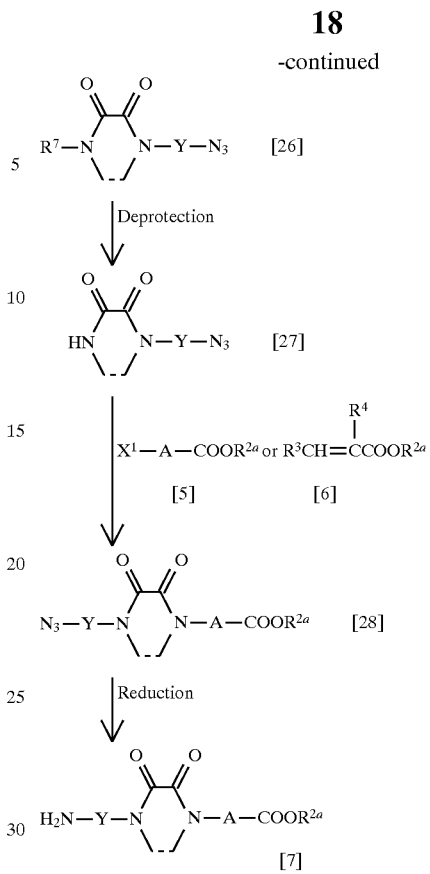
[Production process D]
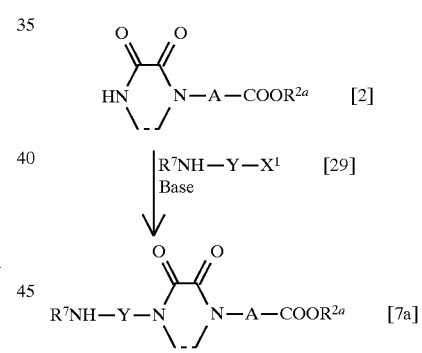
[Production process E]
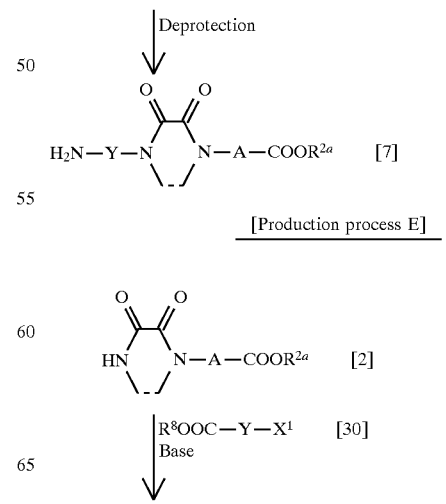

-continued $R^8OOC-Y-N\underset{\_}{\overset{\_}{\diagup}}N-A-COOR^{2a}$ [14a]

| Deprotection
↓

$HOOC-Y-N\underset{\_}{\overset{\_}{\diagup}}N-A-COOR^{2a}$ [14]

[Production process F]

$H_2N-Y-N\underset{\_}{\overset{\_}{\diagup}}N-A-COOR^{2a}$ [7]

↓ NC—⟨⟩—COOH [31a]  or  NC—⟨⟩—SO₂OH [31b]

↓

$NC-⟨⟩-B^2-Y-N\underset{\_}{\overset{\_}{\diagup}}N-A-COOR^{2a}$ [9a]

[Production process G]

$NC-⟨⟩-B^3-Y-N\underset{\_}{\overset{\_}{\diagup}}NH$ [4a]

↓ $X^1-A-COOR^{2a}$ or $R^3CH=\overset{R^4}{C}COOR^{2a}$
   Base [5]                 Base [6]

↓

$NC-⟨⟩-B^3-Y-N\underset{\_}{\overset{\_}{\diagup}}N-A-COOR^{2a}$ [9]

↑ $NC-⟨⟩-B^3-Y-X^1$
   Base [3c]

$HN\underset{\_}{\overset{\_}{\diagup}}N-A-COOR^{2a}$ [2]

wherein $R^{1b}$ represents an amidino group; $R^7$ represents an amino-protecting group; $R^8$ represents a carboxyl-protecting group; and $R^1$, $R^{1a}$, $R^{2a}$, $R^3$, $R^4$, $R^5$, $R^6$, X, $X^1$, A, $B^1$, $B^2$, $B^3$ and Y are as defined above.

Next, production processes are explained below.
[Production process A]

The compound of the general formula [2] can be obtained by reacting a compound of the general formula [18] with a compound of the general formula [5] or [6] in the presence of a base in the same manner as explained in production process 2, to obtain a compound of the general formula [19], and then subjecting this compound to a well-known reaction for removing the protecting group.

The compound of the general formula [4] can be obtained by reacting a compound of the general formula [18] with the compound of the general formula [3a] in the presence of a base in the same manner as explained in production process 1, to obtain a compound of the general formula [20], and then subjecting this compound to a well-known reaction for removing the protecting group.
[Production process B]

A compound of the general formula [23] is obtained by reacting a compound of the general formula [21] with a compound of the general formula [24] in the presence of a base such as potassium carbonate, potassium tert-butoxide or the like.

Then, a compound of the general formula [3b] is obtained by a conventional process, for example, (a) a process of reacting the compound of the general formula [23] with hydrogen chloride in an alcohol such as methanol, ethanol or the like, and then with ammonium chloride, ammonium acetate, ammonia or the like, or (b) a process of reacting the compound of the general formula [23] with hydrogen sulfide and a base such as triethylamine or the like in pyridine to obtain a thioamide, methylating the thioamide with methyl iodide in acetone, and then reacting the methylated thioamide with ammonium acetate. Subsequently, the amidino group of the compound of the general formula [3b] is protected by a conventional method, whereby the compound of the general formula [3a] can be obtained.
[Production process C]

A compound of the general formula [25] is obtained by reacting a compound of the general formula [18] with a compound of the general formula [24] in the presence of a base.

A compound of the general formula [26] is obtained by reacting the compound of the general formula [25] with an agent for azidation, such as sodium azide or the like.

A compound of the general formula [27] is obtained by subjecting the compound of the general formula [26] to a well-known reaction for removing the amino-protecting group.

A compound of the general formula [28] is obtained by reacting the compound of the general formula [27] with a compound of the general formula [5] or [6] in the presence of a base.

Subsequently, the compound of the general formula [28] is subjected to a well-known reduction reaction such as a catalytic reduction reaction using, e.g., a palladium catalyst, whereby the compound of the general formula [7] can be produced.

Any solvent may be used in these reactions so long as it has no undesirable influence on the reactions. The solvent includes, for example, amides such as N,N-dimethylformamide, N,N-dimethylacetamide and the like; and ethers such as tetrahydrofuran, dioxane and the like. The base used in the reactions includes, for example, sodium hydride, metallic sodium, potassium tert-butoxide, sodium carbonate, potassium carbonate, DBU and the like.
[Production process D]

The compound of the general formula [7] can be obtained by reacting the compound of the general formula [2] with a compound of the general formula [29] in the presence of a base to obtain a compound of the general formula [7a], and then subjecting this compound to a well-known reaction for removing the amino-protecting group.

Examples of the base and solvent which are used in these reactions are the same bases and solvents as those exemplified in production process C.

[Production process E]

The compound of the general formula [14] can be obtained by reacting the compound of the general formula [2] with a compound of the general formula [30] in the presence of a base to obtain a compound of the general formula [14a], and then subjecting this compound to a well-known reaction for removing the carboxyl-protecting group.

Examples of the base and solvent which are used in these reactions are the same bases and solvents as those exemplified in production process C.

[Production process F]

A compound of the general formula [9a] can be produced by reacting the compound of the general formula [7] with a compound of the general formula [31a] or its reactive derivative substituted at the carboxyl group or with a compound of the general formula [29b] or its reactive derivative substituted at the sulfo group in the same manner as explained in production process 3.

[Production process G]

The compound of the general formula [9] can be obtained by reacting a compound of the general formula [4a] with a compound of the general formula [5] or [6] in the presence of a base in the same manner as explained in production process 2, or reacting the compound of the general formula [2] with a compound of the general formula [3c] in the presence of a base in the same manner as explained in production process 1.

In the production processes explained above, when the compound of the general formula [9] has an asymmetric center, an optically active salt of the compound of the general formula [9] can be produced by reacting an optically active amine such as d- or l-phenylethylamine, cinchonine, cinchonidine, brucine or the like with a free acid of the compound of the general formula [9] to form a diastereomeric salt, and then recrystallizing the diastereomeric salt from a suitable solvent. It is also possible to convert the thus obtained salt to a free carboxylic acid by removing its base by a per se well-known method.

The compound of the general formula [18] can be synthesized according to, for example, any of the processes described in Yakugaku Zasshi, Vol. 99, No. 9, pp. 929–935 (1979), JP-B-3-57913, etc.

When any of the compounds of the general formulas [1a], [1b], [1c], [1d], [1e], [2], [3a], [3b], [3c], [4], [5], [6], [7], [7a], [8a], [8b], [9], [12], [14], [14a], [15], [17], [19], [20] and [23] to [30] or their salts in the production processes described above has isomers (for example, optical isomers, geometrical isomers, tautomers and the like), these isomers may be used. In addition, the compounds or their salts may be used in the form of a solvate or hydrate or in any of various crystal forms.

When any of the compounds of the general formula [1a], [1b], [1c], [1d], [1e], [2], [3a], [3b], [3c], [4], [5], [6], [7], [7a], [9], [10], [12], [14a], [17] and [19] to [30] or their salts has an amino, carboxyl or hydroxyl group, it is possible to protect the group with a conventional protecting group previously and remove the protecting group by a per se well-known method after completion of the reaction.

The thus obtained compound of the general formula [1] or salt thereof can be isolated and purified according to one or more conventional operations such as extraction, crystallization and/or column chromatography and the like.

When the compound of the present invention is used as a pharmaceutical, it may be properly mixed with a preparation adjuvant such as an excipient, a carrier or a diluent which is usually used for formulation into a pharmaceutical form. The compound can be administered orally or parenterally in the form of tablets, capsules, a powder, a syrup, granules, pills, a suspension, an emulsion, a solution, a powdery formulation, a suppository, an ointment, an injection or the like. The administration route, dose and number of administrations may be properly chosen depending on the age, body weight and symptom of a patient. Usually, the compound may be administered to an adult in a dose of 0.1 to 1,000 mg per day in one portion or several portions orally or parenterally (for example, by injection, drip infusion or intrarectal administration).

Next, the pharmacological activity of typical compounds of the present invention is explained below.

(1) Inhibitory effect on human platelet aggregation

A mixture of blood collected from a human elbow vein and a 3.8% sodium citrate solution in the ratio of 9:1 (v/v) was centrifuged at room temperature to obtain platelet-rich plasma and platelet-poor plasma. Then, the platelet-rich plasma was diluted with the platelet-poor plasma to adjust the number of platelets to $5 \times 10^8$ platelets/ml. To 150 $\mu$l of the diluted platelet-rich plasma was added 18.75 $\mu$l of a solution of each test compound in physiological saline, and the resulting mixture was incubated with stirring at 37° C. After 3 minutes, 18.75 $\mu$l of adenosine 5'-diphosphate (ADP) (final concentration: 3 $\mu$M) was added to the mixture and a change in the intensity of transmitted light caused by the aggregation was recorded with the lapse of time with an aggreometer.

The degree of agglutination in the case of adding only physiological saline was taken as 100% aggregation, and 50% inhibitory concentration ($IC_{50}$) was defined as a concentration of the test compound at which 50% aggregation took place. Table 1 shows the results obtained.

TABLE 1

| Example No. | 50% inhibitory concentration ($\mu$M) |
| --- | --- |
| 10 | 5.0 |
| 13 | 10.0 |
| 15 | 4.7 |
| 16 | 2.2 |
| 17 | 42.0 |
| 19 | 0.14 |
| 20 | 0.9 |
| 58 | 0.054 |
| 59 | 0.37 |
| 61 | 0.12 |
| 62 | 3.2 |
| 64 | 0.16 |
| 65 | 0.29 |
| 66 | 0.14 |
| 67 | 0.57 |
| 77 | 0.14 |
| 78 | 0.15 |
| 79 | 3.5 |
| 82 | 0.48 |
| 83 | 1.1 |
| 85 | 0.29 |
| 86 | 0.63 |
| 87 | 0.53 |
| 88 | 3.4 |
| 97 | 0.56 |
| 99 | 2.1 |
| 102 | 0.5 |
| 103 | 1.9 |
| 104 | 0.8 |

TABLE 1-continued

| Example No. | 50% inhibitory concentration ($\mu$M) |
|---|---|
| 105(2) | 0.95 |
| 106 | 1.0 |

2. Acute toxicity

A solution of the compound of Example 58 in physiological saline was intravenously administered to a group consisting of 5 ddY strain male mice (average body weight: 27.5 g) each, in the tails, whereby the acute toxicity of the compound was investigated. As a result, no mouse died at a dose of the test compound of 300 mg/kg.

BEST MODE FOR CARRYING OUT THE INVENTION

The present invention is illustrated with reference to the following reference examples and examples, which should not be construed as limiting the scope of the invention.

In the reference examples and the examples, the mixing ratios in the eluents are all by volume, and Silica gel 60, No. 7734 (mfd. by MERCK & CO., INC.) was used as a carrier in the column chromatography and LC-SORB SP-B-ODS (mfd. by Chemco Scientific Co., Ltd.) was used as a carrier in the reversed phase column chromatography. The symbols used in the reference examples and the examples have the following meanings:

$d_1$ -TFA: a trifluoroacetic acid-$d_1$,
$d_6$-DMSO: a dimethylsulfoxide-$d_6$,
t-Bu: tert-butyl,
DPM: diphenylmethyl,
BOC: tert-butoxycarbonyl,
Cbz: benzyloxycarbonyl.

Reference Example 1

1-Bromo-3-(4-cyanophenoxy)propane

In 50 ml of dimethyl sulfoxide was dissolved 10 g of 4-cyanophenol, followed by adding thereto 23 g of potassium carbonate at room temperature. The resulting mixture was stirred at the same temperature for 5 minutes and then 64 ml of 1,3-dibromopropane was added thereto, followed by stirring at room temperature for 12 hours. Subsequently, the reaction mixture was added to a mixed solvent of 200 ml of ethyl acetate and 100 ml of water, after which the organic layer was separated and the aqueous layer was extracted with 50 ml of ethyl acetate. The combined organic layer was washed successively with a 1N aqueous sodium hydroxide solution, water and a saturated aqueous sodium chloride solution and dried over anhydrous magnesium sulfate. The solvent was distilled off under reduced pressure and the resulting residue was purified by a silica gel column chromatography (eluent; hexane: ethyl acetate=5:1) to obtain 5.1 g of 1-bromo-3-(4-cyanophenoxy)-propane as a colorless oil.

IR (neat) cm$^{-1}$: $\nu_{CN}$ 2225.

NMR (CDCl$_3$) $\delta$ values: 2.1–2.6 (2H, m), 3.58 (2H, t, J=6 Hz), 4.16 (2H, t, J=6 Hz), 6.94 (2H, d, J=9 Hz), 7.57 (2H, d, J=9 Hz).

The following compounds were obtained in the same manner as above.

1-Bromo-2-(4-cyanophenoxy)ethane

IR (KBr) cm$^{-1}$: $\nu_{CN}$ 2225.

NMR (CDCl$_3$) $\delta$ values: 3.64 (2H, t, J=6 Hz), 4.34 (2H, t, J=6 Hz), 6.95 (2H, d, J=9 Hz), 7.60 (2H, d, J=9 Hz).

1-Bromo-4-(4-cyanophenoxy)butane

IR (neat) cm$^{-1}$: $\nu_{CN}$ 2225.

NMR (CDCl$_3$) $\delta$ values: 1.9–2.2 (4H, m), 3.3–3.6 (2H, m), 4.04 (2H, t, J=5.5 Hz), 6.92 (2H, d, J=9 Hz), 7.58 (2H, d, J=9 Hz).

1-Bromo-5-(4-cyanophenoxy)pentane

IR (KBr) cm$^{-1}$: $\nu_{CN}$ 2225.

NMR (CDCl$_3$) $\delta$ values: 1.4–2.5 (6H, m), 3.44 (2H, t, J=6 Hz), 4.02 (2H, t, J=6 Hz), 6.93 (2H, d, J=9 Hz), 7.57 (2H, d, J=9 Hz).

Reference Example 2

1-Bromo-3-(4-amidinophenoxy)propane hydrochloride

In 200 ml of absolute ethanol was dissolved 20.0 g of 1-bromo-3-(4-cyanophenoxy)propane, and hydrogen chloride gas was introduced thereinto at 0°–5° C. until the solution was saturated therewith. After overnight standing at room temperature, the solvent was distilled off under reduced pressure and 100 ml of diisopropyl ether and 50 ml of hexane were added to the resulting residue. The solid was collected by filtration and dried over anhydrous phosphorus pentaoxide under reduced pressure to obtain 21.3 g of 1-bromo-3-(4 -ethoxyiminophenoxy)propane hydrochloride. The hydrochloride was suspended in 120 ml of ethanol, followed by adding thereto 35 ml of a 4.8N solution of ammonia in ethanol, and the resulting mixture was heated under reflux for 3 hours and then cooled to room temperature. The solvent was distilled off under reduced pressure and 25 ml of isopropanol was added to the resulting solid, after which the crystals were collected by filtration to obtain 17.9 g of 1-bromo-3-(4-amidinophenoxy)-propane hydrochloride as colorless crystals.

NMR (d$_6$-DMSO) $\delta$ values: 2.0–2.6 (2H, m), 3.6–4.0 (2H, m), 4.25 (2H, t, J=6 Hz), 7.21 (2H, d, J=9 Hz), 7.99 (2H, d, J=9 Hz), 8.8–9.9 (4H, m).

The following compounds were obtained in the same manner as above.

1-Bromo-2-(4-amidinophenoxy)ethane hydrochloride

NMR (d$_6$-DMSO) $\delta$ values: 3.7–4.5 (4H, m), 7.18 (2H, d, J=9 Hz), 7.90 (2H, d, J=9 Hz), 9.14 (4H, brs).

1-Bromo-4-(4-amidinophenoxy)butane hydrochloride

NMR (D$_2$O) $\delta$ values: 1.7–2.0 (4H, m), 3.3–3.7 (2H, m), 3.8–4.1 (2H, m), 6.86 (2H, d, J=9 Hz), 7.63 (2H, d, J=9 Hz).

1-Bromo-5-(4-amidinophenoxy)pentane hydrochloride

NMR (d$_6$-DMSO) $\delta$ values: 1.3–2.9 (6H, m), 3.3–4.5 (4H, m), 7.14 (2H, d, J=8 Hz), 7.93 (2H, d, J=8 Hz), 8.7–9.8 (4H, m).

Reference Example 3

1-Bromo-3-(4-benzyloxycarbonylamidinophenoxy)-propane

In a mixed solvent of 175 ml of a saturated aqueous sodium carbonate solution, 90 ml of water and 350 ml of methylene chloride was dissolved 17.5 g of 1-bromo-3-(4-amidinophenoxy)propane hydrochloride, and 8.5 ml of benzyloxycarbonyl chloride was added thereto under ice-cooling. The resulting mixture was vigorously stirred at the same temperature for 30 minutes and then at room temperature for 4 hours, after which the organic layer was separated and the aqueous layer was extracted with 150 ml of methylene chloride. The combined organic layer was washed with water and then a saturated aqueous sodium chloride solution, dried over anhydrous magnesium sulfate, and then distilled under reduced pressure to remove the solvent. Hexane was added to the resulting residue and the crystals were collected by filtration and dried to obtain 19.6 g of 1-bromo-3-(4-benzyloxycarbonylamidinophenoxy)propane as colorless crystals.

IR (KBr) cm$^{-1}$: $v_{C=O}$ 1660.

NMR (CDCl$_3$) δ values: 2.0–2.6 (2H, m), 3.4–3.9 (2H, m), 4.10 (2H, t, J=6 Hz), 5.19 (2H, s), 6.86 (2H, d, J=9 Hz), 7.1–8.6 (9H, m).

The following compounds were obtained in the same manner as above.

1-Bromo-2-(4-benzyloxycarbonylamidinophenoxy)ethane
IR (KBr) cm$^{-1}$: $v_{C=O}$ 1665.

NMR (CDCl$_3$) δ values: 3.61 (2H, t, J=6 Hz), 4.30 (2H, t, J=6 Hz), 5.20 (2H, s), 6.89 (2H, d, J=9 Hz), 7.0–9.4 (9H, m).

1-Bromo-4-(4-benzyloxycarbonylamidinophenoxy)butane
IR (KBr) cm$^{-1}$: $v_{C=O}$ 1665.

NMR (CDCl$_3$) δ values: 1.8–2.1 (4H, m), 3.45 (2H, t, J=6Hz), 4.00 (2H, t, J=6Hz), 5.19 (2H, s), 6.86 (2H, d, J=9 Hz), 7.0–9.2 (9H, m).

1-Bromo-5-(4-benzyloxycarbonylamidinophenoxy)pentane
IR (KBr) cm$^{-1}$: $v_{C=O}$ 1665.

NMR (CDCl$_3$) δ values: 1.3–2.4 (6H, m), 3.44 (2H, t, J=6 Hz), 3.95 (2H, t, J=6 Hz), 5.18 (2H, s), 6.83 (2H, d, J=9 Hz), 7.1–8.5 (9H, m).

Reference Example 4

4-[3-(4-Benzyloxycarbonylamidinophenoxy)-propyl]-1-(2,4-dimethoxybenzyl)-2,3-dioxopiperazine In 10 ml of N,N-dimethylformamide was dissolved 1.00 g of 1-(2,4-dimethoxybenzyl)-2,3-dioxopiperazine, and 0.17 g of sodium hydride (60%, oil) was added to the solution, followed by stirring at 50° C. for 30 minutes. Then, the reaction mixture was cooled to room temperature, after which 1.48 g of 1-bromo-3-(4-benzyloxycarbonylamidinophenoxy)propane was added thereto and the resulting mixture was stirred overnight at the same temperature. The solvent was distilled off under reduced pressure and the resulting residue was purified by a silica gel column chromatography (eluent; chloroform:methanol=20:1) to obtain 1.76 g of 4-(3-(4-benzyloxycarbonylamidinophenoxy)propyl]-1-(2,4-dimethoxybenzyl)-2,3-dioxopiperazine as colorless crystals.

IR (KBr) cm$^{-1}$: $v_{C=O}$ 1665.

NMR (CDCl$_3$) δ values: 1.7–2.5 (2H, m), 3.2–4.2 (14H, m), 4.60 (2H, s), 5.18 (2H, s), 6.3–6.6 (2H, m), 6.7–8.9 (12H, m).

4-[4-(4-Benzyloxycarbonylamidinophenoxy)-butyl]-1-(2,4-dimethoxybenzyl)-2,3-dioxopiperazine was obtained in the same manner as above except for using 1-bromo-4-(4-benzyloxycarbonylamidinophenoxy)butane.

IR (KBr) cm$^{-1}$: Vc=o 1670.

NMR (CDCl$_3$) δ values: 1.5–2.1 (4H, m), 3.2–4.4 (14H, m), 4.59 (2H, s), 5.17 (2H, s), 6.2–6.6 (2H, m), 6.82 (2H, d, J=9 Hz), 7.1–8.6 (10H, m).

Reference Example 5

1-[3-(4-tert-Butoxycarbonylamidinophenoxy)-propyl]-2,3-dioxopiperazine

In 16.5 ml of anisole was dissolved 8.25 g of 4-[3-(4-benzyloxycarbonylamidinophenoxy)propyl]-1-(2,4-dimethoxybenzyl)-2,3-dioxopiperazine, and 33 ml of trifluoroacetic acid was added to the solution, followed by refluxing for 5 hours. After cooling, the solvent was distilled off under reduced pressure. To the resulting residue was added 40 ml of ethyl acetate, and stirred for 30 minutes, after which the precipitate was collected by filtration and dried to obtain 8.23 g of 4-[3-(4-amidinophenoxy)propyl]-2,3-dioxopiperazine trifluoro-acetate. Then, the compound obtained was dissolved in a mixed solvent of 182 ml of dioxane and 82 ml of water, followed by adding thereto 8.37 g of sodium carbonate and 3.62 g of di-tert-butyl dicarbonate, and the resulting mixture was stirred at room temperature for 5 hours. The solvent was distilled off under reduced pressure and 80 ml of ethyl acetate and 80 ml of water were added to the resulting residue and stirred for 30 minutes. The crystals precipitated were collected by filtration and dried to obtain 4.27 g of 1-[3-(4-tert-butoxycarbonyl-amidinophenoxy)propyl]-2,3-dioxopiperazine as colorless crystals.

IR (KBr) cm$^{-1}$: $v_{C=O}$ 1715, 1680, 1625.

NMR (d$_6$-DMSO) δ values: 1.47 (9H, s), 1.7–2.4 (2H, m), 3.2–4.3 (8H, m), 6.91 (2H, d, J=9 Hz), 7.8–9.5 (5H, m).

Reference Example 6

1-[4-(4-Benzyloxycarbonylamidinophenoxy)-butyl]-2,3-dioxopiperazine (1) In 3.4 ml of anisole was dissolved 1.7 g of 4-[4-(4-benzyloxycarbonylamidinophenoxy)butyl]-1-(2,4-dimethoxybenzyl)-2,3-dioxopiperazine, and 6.8 ml of trifluoroacetic acid was added to the solution, followed by refluxing for 5 hours. After cooling, the solvent was distilled off under reduced pressure. To the resulting residue was added 10 ml of ethyl acetate, and stirred for 30 minutes, after which the precipitate was collected by filtration and dried to obtain 1.2 g of 4-[4-(4-amidinophenoxy)butyl]-2,3-dioxopiperazine trifluoroacetate.

(2) The compound obtained was dissolved in a mixed solvent of 20 ml of tetrahydrofuran and 10 ml of water, and 0.67 g of sodium carbonate was added thereto, followed by stirring at room temperature for 30 minutes. To the resulting solution was added 0.27 ml of benzyloxycarbonyl chloride and the resulting mixture was stirred at the same temperature for 5 hours. Then, 20 ml of ethyl acetate and 10 ml of water were added to the reaction mixture, after which the organic layer was separated and the aqueous layer was extracted with 20 ml of ethyl acetate. The combined organic layer was washed with water and then a saturated aqueous sodium chloride solution and dried over anhydrous magnesium sulfate, after which the solvent was distilled off under reduced pressure to obtain 0.42 g of 1-[4-(4-benzyloxycarbonyl-amidinophenoxy)butyl]-2,3-dioxopiperazine as an oil.

IR (KBr) cm$^{-1}$: $v_{C=O}$ 1695, 1665.

NMR (CDCl$_3$) δ values: 1.4–2.1 (4H, m), 3.0–4.3 (8H, m), 5.16 (2H, s), 6.82 (2H, d, 9 Hz), 7.1–9.5 (10H, m).

Reference Example 7

Methyl [4-(2,4-dimethoxybenzyl)-2,3-dioxopiperazin-1-yl]acetate

A mixture of 10.0 g of 1-(2,4-dimethoxy-benzyl)-2,3-dioxopiperazine, 1.66 g of sodium hydride (60%, oil) and 100 ml of N,N-dimethylformamide was stirred at 50° C. for 30 minutes and then cooled to room temperature. To the reaction mixture was added 3.6 ml of methyl bromoacetate, after which the resulting mixture was stirred at the same temperature for 30 minutes and added to a mixed solvent of 200 ml of ethyl acetate and 200 ml of ice water, and the pH was adjusted to 2 with 2N hydrochloric acid. The organic layer was separated and the aqueous layer was extracted with five 50-ml portions of ethyl acetate. The combined organic layer was washed with 50 ml of water and then a saturated aqueous sodium chloride solution and dried over anhydrous magnesium sulfate. The solvent was distilled off under reduced pressure and the resulting residue was purified by a silica gel column chromatography (eluent; chloroform: methanol=10:1) to obtain 10.7 g of methyl [4-(2,4-dimethoxybenzyl)-2,3-dioxopiperazin-1-yl]acetate as a colorless oil.

IR (KBr) cm$^{-1}$: $\nu_{C=O}$ 1740, 1670.

NMR (CDCl$_3$) δ values: 3.1–4.1 (13H, m), 4.23 (2H, s), 4.64 (2H, s), 6.1–6.6 (2H, m), 6.9–7.4 (1H, m).

The following compounds were obtained in the same manner as above.

Methyl [4-(2,4-dimethoxybenzyl)-1,2,3,4-tetrahydro-2,3-dioxopyrazin-1-yl]acetate IR (KBr) cm$^{-1}$: $\nu_{C=O}$ 1745, 1690, 1645.

NMR (d$_6$-DMSO) δ values: 3.69 (3H, s), 3.76 (3H, s), 3.80 (3H, s), 4.54 (2H, s), 4.80 (2H, s), 6.3–6.7 (4H, m), 7.0–7.2 (1H, m).

Ethyl 4-[4-(2,4-dimethoxybenzyl)-2,3-dioxopiperazin-1-yl]butyrate

IR (KBr) cm$^{-1}$; $\nu_{C=O}$ 1730, 1670.

NMR (CDCl$_3$) δ values: 1.24 (3H, t, J=7 Hz), 1.7–3.1 (4H, m), 3.3–4.0 (12H, m), 4.12 (2H, q, J=7 Hz), 4.62 (2H, s), 6.3–6.6 (2H, m), 7.1–7.4 (1H, m).

Reference Example 8

Methyl 3-[4-(2,4-dimethoxybenzyl)-2,3-dioxopiperazin-1-yl]propionate

A mixture of 1.0 g of 1-(2,4-dimethoxybenzyl)-2,3-dioxopiperazine, 0.28 ml of 1,8-diazabicyclo[5.4.0]-undec-7-ene, 0.34 ml of methyl acrylate and 10 ml of N,N-dimethylformamide was stirred at room temperature for 12 hours. Then, the solvent was distilled off under reduced pressure, after which the resulting residue was added to a mixed solvent of 30 ml of ethyl acetate and 30 ml of water, and the pH was adjusted to 3 with 2N hydrochloric acid. The organic layer was separated and the aqueous layer was extracted with three 30-ml portions of ethyl acetate. The combined organic layer was washed with water and then a saturated aqueous sodium chloride solution and dried over anhydrous magnesium sulfate. The solvent was distilled off under reduced pressure and the resulting residue was purified by a silica gel column chromatography (eluent; chloroform: methanol=20:1) to obtain 0.68 g of methyl 3-[4-(2,4-dimethoxybenzyl)-2,3-dioxopiperazin-1-yl]propionate as a colorless oil.

IR (neat) cm$^{-1}$: $\nu_{C=O}$ 1730, 1680.

NMR (CDCl$_3$) δ values: 2.68 (2H, t, J=6 Hz), 3.2–4.0 (15H, m), 4.61 (2H, s), 6.3–6.6 (2H, m), 7.0–7.4 (1H, m).

Benzyl 2-[(1,3-benzodioxol-5-yl)methyl]-3-[4-(2,4-dimethoxybenzyl)-2,3-dioxopiperazin-1-yl]propionate was obtained in the same manner as above except for using benzyl 2-[(1,3-benzodioxol-5-yl)methyl]acrylate in place of methyl acrylate.

IR (neat) cm$^{-1}$: $\nu_{C=O}$ 1730, 1675.

NMR (CDCl$_3$) δ values: 3.1–3.4 (6H, m), 3.7–3.9 (9H, m), 4.54 (2H, s), 5.01 (2H, s), 5.89 (2H, s), 6.4–6.8 (5H, m), 7.1–7.5 (6H, m).

Reference Example 9

Methyl (2,3-dioxopiperazin-1-yl)acetate

A mixture of 10.5 g of methyl [4-(2,4-dimethoxybenzyl)-2,3-dioxopiperazin-1-yl]acetate, 42 ml of trifluoroacetic acid and 21 ml of anisole was refluxed for 4 hours. The reaction mixture was cooled to room temperature and then distilled under reduced pressure to remove the solvent. The resulting residue was purified by a silica gel column chromatography (eluent; chloroform: methanol=6:1) to obtain 4.5 g of methyl (2,3-dioxopiperazin-1-yl)acetate as colorless crystals.

IR (KBr) cm$^{-1}$: $\nu_{C=O}$ 1745, 1680.

NMR (d$_6$-DMSO) δ values: 3.2–3.6 (4H, m), 3.67 (3H, s), 4.21 (2H, s), 8.51 (1H, brs).

The following compounds were obtained in the same manner as above.

Methyl (1,2,3,4-tetrahydro-2,3-dioxopyrazin-1-yl)-acetate

IR (KBr) cm$^{-1}$: $\nu_{C=O}$ 1750, 1685, 1650.

NMR (d$_6$-DMSO) δ values: 3.74 (3H, s), 4.56 (2H, s), 6.2–6.8 (3H, m).

Ethyl 4-(2,3-dioxopiperazin-1-yl)butyrate

IR (neat) cm$^{-1}$: νC=O 1735, 1655.

NMR (CDCl$_3$) δ values: 1.24 (3H, t, J=8 Hz), 1.6–2.7 (4H, m), 3.3–3.9 (6H, m), 4.12 (2H, q, J=8 Hz), 8.66 (1H, brs).

Methyl 3-(2,3-dioxopiperazin-1-yl)propionate

IR (neat) cm$^{-1}$: $\nu_{C=O}$ 1735, 1665.

NMR (d$_6$-DMSO) δ values: 2.4–2.8 (2H, m), 3.1–3.8 (9H, m), 8.55 (1H, brs).

Benzyl 2-[(1,3-benzodioxol-5-yl)methyl]-3-(2,3-dioxopiperazin-1-yl)propionate

IR (KBr) cm$^{-1}$: $\nu_{C=O}$ 1730, 1670.

NMR (CDCl$_3$) δ values: 2.6–4.4 (9H, m), 5.03 (2H, s), 5.87 (2H, s), 6.4–6.8 (3H, m), 7.0–7.6 (5H, m), 8.47 (1H, brs).

Reference Example 10

1-[3-(4-Cyanophenoxy)propyl]-4-(2,4-dimethoxybenzyl)-2,3-dioxopiperazine

This compound was obtained in the same manner as in Reference Example 4.

IR (KBr) cm$^{-1}$: $\nu_{CN}$ 2230, $\nu_{C=O}$ 1680.

NMR (CDCl$_3$) δ values: 1.9–2.4 (2H, m), 3.4–3.7 (6H, m), 3.08 (6H, s), 4.05 (2H, t, J=6 Hz), 4.62 (2H, s), 6.3–6.6 (2H, m), 6.93 (2H, d, J=8.5 Hz), 7.26 (1H, d, J=9 Hz), 7.55 (2H, d, J=8.5 Hz).

Reference Example 11

1-[3-(4-Cyanophenoxy)propyl]-2,3-dioxopiperazine

This compound was obtained in the same manner as in Reference Example 6 (1).

IR (KBr) cm$^{-1}$: $\nu_{CN}$ 2220, $\nu_{C=O}$ 1670.

NMR (d$_6$-DMSO) δ values: 1.6–2.3 (2H, m), 3.1–3.8 (6H, m), 3.9–4.5 (2H, m), 7.09 (2H, d, J=9 Hz), 7.76 (2H, d, J=9 Hz), 8.55 (1H, brs).

Reference Example 12

1-(2-Bromoethyl)-4-(2,4-dimethoxybenzyl)-2,3-dioxopiperazine

In 100 ml of N,N-dimethylformamide was suspended 10 g of 1-(2,4-dimethoxybenzyl)-2,3-dioxopiperazine, and 1.67 g of sodium hydride (60%, oil) was added to the suspension, followed by stirring at 50° C. for 1 hour. Then, the reaction mixture was cooled to room temperature, after which 16.5 ml of 1,2-dibromoethane was added thereto and the resulting mixture was stirred at the same temperature for 4 hours. After the solvent was distilled off under reduced pressure, a mixed solvent of 100 ml of ethyl acetate and 60 ml of water was added to the residue and the pH was adjusted to 3 with 2N hydrochloric acid. The organic layer was separated and the aqueous layer was extracted with 50 ml of ethyl acetate. The combined organic layer was washed with 20 ml of water and then a saturated aqueous sodium chloride solution and dried over anhydrous magnesium sulfate. The solvent was distilled off under reduced pressure and the resulting residue was purified by a silica gel column chromatography (eluent; chloroform: methanol=30:1) to obtain 6.1 g of 1-(2-bromoethyl)-4-(2,4-dimethoxybenzyl)-2,3-dioxopiperazine as colorless crystals.

IR (KBr) cm$^{-1}$: $v_{C=O}$ 1685, 1670.

NMR (CDCl$_3$) δ values: 3.4–4.0 (14H, m), 4.63 (2H, s), 6.3–6.6 (2H, m), 7.1–7.4 (1H, m).

The following compound was obtained in the same manner as above.

1-(3-Bromopropyl)-4-(2,4-dimethoxybenzyl)-2,3-dioxopiperazine

IR (KBr) cm$^{-1}$: $v_{C=O}$ 1675.

NMR (CDCl$_3$) δ values: 1.9–2.4 (2H, m), 3.3–4.0 (14H, m), 4.63 (2H, s), 6.3–6.6 (2H, m), 7.1–7.3 (1H, m).

Reference Example 13

1-(2-Azidoethyl)-4-(2,4-dimethoxybenzyl)-2,3-dioxopiperazine

A mixture of 4.5 g of 1-(2-bromoethyl)-4-(2,4-dimethoxybenzyl)-2,3-dioxopiperazine, 1.03 g of sodium azide and 45 ml of N,N-dimethylformamide was stirred at 80° C. for 1 hour and then distilled under reduced pressure to remove the solvent. To the resulting residue were added 60 ml of ethyl acetate and 30 ml of water, and the pH was adjusted to 3 with 2N hydrochloric acid. The organic layer was separated and the aqueous layer was extracted with two 30-ml portions of ethyl acetate. The combined organic layer was washed with 20 ml of water and then a saturated aqueous sodium chloride solution and dried over anhydrous magnesium sulfate. After the solvent was distilled off under reduced pressure, 5 ml of diisopropyl ether and 5 ml of diethyl ether were added to the resulting residue and the crystals were collected by filtration to obtain 3.7 g of 1-(2-azidoethyl)-4-(2,4-dimethoxybenzyl)-2,3-dioxopiperazine as colorless crystals.

IR (KBr) cm$^{-1}$: $v_{C=O}$ 1675.

NMR (CDCl$_3$) δ values: 3.4–4.0 (14H, m), 4.63 (2H, s), 6.3–6.6 (2H, m), 7.1–7.4 (1H, m).

1-(3-Azidopropyl)-4-(2,4-dimethoxybenzyl)-2,3-dioxopiperazine was obtained in the same manner as above.

IR (neat) cm$^{-1}$: $v_{C=O}$ 1670.

NMR (CDCl$_3$) δ values: 1.6–2.1 (2H, m), 3.2–3.9 (14H, m), 4.62 (2H, s), 6.4–6.6 (2H, m), 7.2–7.4 (1H, m).

Reference Example 14

1-(2-Azidoethyl)-2,3-dioxopiperazine

A mixture of 3.65 g of 1-(2-azidoethyl)-4-(2,4-dimethoxybenzyl)-2,3-dioxopiperazine, 14.6 ml of trifluoroacetic acid and 7.3 ml of anisole was refluxed for 2 hours. The solvent was distilled off under reduced pressure and the resulting residue was purified by a silica gel column chromatography (eluent; chloroform: methanol=20:1) to obtain 1.8 g of 1-(2-azidoethyl)-2,3-dioxopiperazine as an oil.

IR (neat) cm$^{-1}$: $v_{C=O}$ 1665.

NMR (d$_6$-DMSO) δ values; 3.1–3.8 (8H, m), 8.63 (1H, brs).

1-(3-Azidopropyl)-2,3-dioxopiperazine was obtained as an oil in the same manner as above.

IR (neat) cm$^{-1}$: vC=O 1670.

NMR (CDCl$_3$) δ values: 1.7–2.1 (2H, m), 3.2–3.9 (8H, m), 8.82 (1H, brs).

Reference Example 15

Diphenylmethyl 3-[4-(2-azidoethyl)-2,3-dioxopiperazin-1-yl]-3-(pyridin-3-yl)propionate A mixture of 0.5 g of 1-(2-azidoethyl)-2,3-dioxopiperazine, 1.72 g of diphenylmethyl 3-(3-pyridyl)-acrylate, 0.2 ml of 1,8-diazabicyclo[5.4.0]undec-7-ene and 2.5 ml of N,N-dimethylformamide was stirred at room temperature for 12 hours. The solvent was distilled off under reduced pressure, after which 30 ml of ethyl acetate and 20 ml of water were added to the resulting residue and the pH was adjusted to 6 with 2N hydrochloric acid. The organic layer was separated and the aqueous layer was extracted with 30 ml of ethyl acetate. The combined organic layer was washed with 20 ml of water and a saturated aqueous sodium chloride solution and dried over anhydrous magnesium sulfate. The solvent was distilled off under reduced pressure and the resulting residue was purified by a silica gel column chromatography (eluent; chloroform: methanol=20:1) to obtain 0.71 g of diphenylmethyl 3-[4-(2-azidoethyl)-2,3-dioxopiperazin-1-yl]-3-(pyridin-3-yl)propionate as a light-brown oil.

IR (KBr) cm$^{-1}$: $v_{C=O}$ 1735, 1675.

NMR (CDCl$_3$) δ values: 3.1–3.8 (10H, m), 5.8–6.2 (1H, m), 6.84 (1H, m), 7.1–7.9 (12H, m), 8.4–8.8 (2H, m).

The following compounds were obtained in the same manner as above.

Diphenylmethyl 3-[4-(3-azidopropyl)-2,3-dioxopiperazin-1-yl]-3-(pyridin-3-yl)propionate IR (KBr) cm$^{-1}$: $v_{C=O}$ 1735, 1675.

NMR (CDCl$_3$) δ values: 1.5–2.0 (2H, m), 2.9–3.9 (10H, m), 5.7–6.1 (1H, m), 6.85 (1H, s), 7.0–8.1 (12H, m), 8.4–8.7 (2H, m).

Benzyl 3-[4-(2-azidoethyl)-2,3-dioxopiperazin-1-yl]propionate

IR (KBr) cm$^{-1}$: $v_{C=O}$ 1730, 1665.

NMR (CDCl$_3$) δ values: 2.74 (2H, t, J=6 Hz), 3.3–3.9 (10H, m), 5.12 (2H, s), 7.34 (5H, s).

Benzyl 3-[4-(3-azidopropyl)-2,3-dioxopiperazin-1-yl]propionate

IR (neat) cm$^{-1}$: $v_{C=O}$ 1735, 1670.

NMR (CDCl$_3$) δ values: 1.7–2.1 (2H, m), 2.74 (2H, t, J=6 Hz), 3.2–3.9 (10H, m), 5.12 (2H, s), 7.35 (5H, s).

Benzyl 3-[4-(2-azidoethyl)-2,3-dioxopiperazin-1-yl]-2-[(1,3-benzodioxol-5-yl)methyl]propionate IR (KBr) cm$^{-1}$: $v_{C=O}$ 1730, 1675.

NMR (CDCl$_3$) δ values: 2.7–3.0 (2H, m), 3.2–3.9 (11H, m), 5.05 (2H, s), 5.90 (2H, s), 6.5–6.8 (3H, m), 7.29 (5H, s).

Benzyl 3-[4-(3-azidopropyl)-2,3-dioxopiperazin-1-yl]-2-[(1,3-benzodioxol-5-yl)methyl]propionate IR (neat) cm$^{-1}$: $v_{C=O}$ 1730, 1680.

NMR (CDCl$_3$) δ values: 1.5–2.3 (2H, m), 2.6–4.1 (13H, m), 5.02 (2H, s), 5.87 (2H, s), 6.5–6.9 (3H, m), 7.1–7.6 (5H, m).

Reference Example 16

Diphenylmethyl 3-[4-(2-aminoethyl)-2,3-dioxopiperazin-1-yl]-3-(pyridin-3-yl)propionate A mixture of 0.7 g of diphenylmethyl 3-[4-(2-azidoethyl)-2,3-dioxopiperazin-1-yl]-3-(pyridin-3-yl)-propionate, 0.13 g of 5% palladium-carbon, 2.8 ml of 1N hydrochloric acid and 7 ml of N,N-dimethylformamide was subjected to hydrogenation at ordinary temperature and atmospheric pressure for 2 hours. After completion of the reaction, the catalyst was filtered off and the filtrate was concentrated under reduced pressure. To the resulting residue were added 5 ml of diethyl ether and 1 ml of ethyl acetate and the resulting mixture was filtered to obtain a white solid. The solid obtained was added to a mixed solvent of 20 ml of methylene chloride and 10 ml of a saturated aqueous sodium hydrogencarbonate solution and stirred for 10 minutes. The organic layer was separated and the aqueous layer was extracted with two 10-ml portions of methylene chloride. The combined organic layer was washed with water and then a saturated aqueous sodium chloride solution. After drying over anhydrous magnesium sulfate, the solvent was distilled off under reduced pressure to obtain 0.2 g of diphenylmethyl 3-[4-(2-amioethyl)-2,3-dioxopiperazin-1-yl]-3-(pyridin-3-yl)-propionate as a brown oil.

IR (neat) cm$^{-1}$: $v_{C=O}$ 1735, 1670.

NMR (CDCl$_3$) δ values: 2.8–3.8 (10H, m), 5.7–6.1 (1H, m), 6.82 (1H, s), 7.0–7.8 (12H, m), 7.9–8.8 (4H, m).

Diphenylmethyl 3-[4-(3-aminopropyl)-2,3-dioxopiperazin-1-yl]-3-(pyridin-3-yl)propionate was obtained as an oil in the same manner as above.

IR (neat) cm$^{-1}$: $v_{C=O}$ 1740, 1680.

NMR (CDCl$_3$) δ values: 1.4–2.0 (2H, m), 3.0–4.1 (12H, m), 5.7–6.1 (1H, m), 6.82 (1H, s), 7.1–8.1 (12H, m), 8.4–8.7 (2H, m).

Reference Example 17

Diphenylmethyl 3-[4-(2-aminoethyl)-2,3-dioxopiperazin-1-yl]-2-[(1,3-benzodioxol-5-yl)methyl]-propionate A mixture of 2.5 g of benzyl 3-[4-(2-azido-ethyl)-2,3-dioxopiperazin-1-yl]-3-[(1,3-benzodioxol-5-yl) methyl] propionate, 0.3 g of 10% palladium-carbon, 0.4 ml of 6N hydrochloric acid and 9 ml of acetic acid was subjected to hydrogenation at ordinary temperature and atmospheric pressure for 2 hours. After completion of the reaction, the catalyst was filtered off and the solvent was distilled off under reduced pressure. In a mixed solvent of 30 ml of chloroform and 10 ml of methanol was dissolved 2.9 g of the resulting residue, followed by adding thereto 6 ml of a 1 M solution of diphenyldiazomethane in ethyl acetate. After stirring at room temperature for 1 hour, 0.4 ml of acetic acid was added thereto to decompose the excess diphenyldiazomethane, and the solvent was distilled off under reduced pressure. To the resulting residue were added 30 ml of methylene chloride and 10 ml of a saturated aqueous sodium hydrogencarbonate solution and the resulting mixture was stirred at room temperature for 10 minutes. The organic layer was separated, washed with water and then a saturated aqueous sodium chloride solution, and then dried over anhydrous magnesium sulfate. The solvent was distilled off under reduced pressure and the resulting residue was purified by a silica gel column chromatography (eluent; chloroform: methanol =10:1) to obtain 1.5 g of diphenylmethyl 3-[4-(2-aminoethyl)-2,3-dioxopiperazin-1-yl]-2-[(1,3-benzodioxol-5-yl)-methyl]propionate as a light-yellow oil.

IR (neat) cm$^{-1}$: $v_{C=O}$ 1735, 1670.

NMR (d$_6$-DMSO) δ values: 2.7–3.0 (2H, m), 3.1–4.2 (13H, m), 5.8–6.1 (2H, m), 6.6–6.9 (4H, m), 7.1–7.4 (10H, m).

The following compounds were obtained in the same manner as above.

Diphenylmethyl 3-[4-(3-aminopropyl)-2,3-dioxopiperazin-1-yl]-2-[(1,3-benzodioxol-5-yl)methyl]-propionate IR (KBr) cm$^{-1}$: $v_{C=O}$ 1735, 1670.

NMR (CDCl$_3$) δ values: 1.4–2.2 (2H, m), 2.4–4.2 (15H, m), 5.7–6.0 (2H, m), 6.5–7.7 (14H, m).

Diphenylmethyl 3-[4-(2-aminoethyl)-2,3-dioxopiperazin-1-yl]propionate

IR (neat) cm$^{-1}$: $v_{C=O}$ 1735, 1670.

NMR (CDCl$_3$) δ values: 2.1–3.9 (14H, m), 6.86 (1H, s), 7.32 (10H, s).

Diphenylmethyl 3-[4-(3-aminopropyl)-2,3-dioxopiperazin-1-yl]propionate

IR (neat) cm$^{-1}$: $v_{C=O}$ 1735, 1665.

NMR (CDCl$_3$) δ values: 1.0–1.6 (2H, m), 2.5–4.4 (12H, m), 4.4–5.2 (2H, m), 6.80 (1H, s), 7.35 (10H, s).

Reference Example 18 tert-Butyl [4-(2-azidoethyl)-2,3-dioxopiperazin-1-yl] acetate

In the same manner as in Reference Example 10, 0.7 g of tert-butyl [4-(2-azidoethyl)-2,3-dioxopiperazin-1-yl]acetate was obtained as colorless crystals from 1.0 g of 1-(2-azidoethyl)-2,3-dioxopiperazine and 1.1 g of tert-butyl bromoacetate.

IR (KBr) cm$^{-1}$: $v_{C=O}$ 1745, 1670.

NMR (CDCl$_3$) δ values: 1.47 (9H, s), 3.5–3.9 (8H, m), 4.15 (2H, s).

Benzyl [4-(2,4-dimethoxybenzyl)-2,3-dioxopiperazin-1-yl]acetate was obtained as a light-yellow oil in the same manner as in Reference Example 10.

IR (neat) cm$^{31}$ $^1$: vhd C=O 1745, 1680.

NMR (CDCl$_3$) δ values: 3.3–3.6 (4H, m), 3.79 (6H, s), 4.26 (2H, s), 4.62 (2H, s), 5.14 (2H, s), 6.3–6.6 (2H, m), 7.1–7.4 (6H, m).

Reference Example 19 tert-Butyl [4-(2-aminoethyl)-2,3-dioxopiperazin-1-yl]acetate hydrochloride tert-Butyl [4-(2-aminoethyl)-2,3-dioxopiperazin-1-yl] acetate hydrochloride was obtained as an oil from tert-butyl [4-(2-azidoethyl)-2,3-dioxopiperazin-1-yl]acetate in the same manner as in Reference Example 16.

IR (KBr) cm$^{-1}$: $v_{C=O}$ 1745, 1670.

NMR (d$_6$-DMSO) δ values: 1.43 (9H, s), 3.6–3.9 (8H, m), 4.10 (2H, s), 8.0–8.7 (3H, brs).

Reference Example 20

Diphenylmethyl (2,3-dioxopiperazin-1-yl) -acetate

A mixture of 10.0 g of benzyl [4-(2,4-dimethoxybenzyl)-2,3-dioxopiperazin- 1-yl]acetate, 40 ml of trifluoroacetic acid and 20 ml of anisole was refluxed for 2 hours. After completion of the reaction, the solvent was distilled off under reduced pressure and 20 ml of ethyl acetate and 10 ml of diethyl ether were added to the resulting residue, and the solid was collected by filtration. The solid obtained was dissolved in a mixed solvent of 9 ml of ethyl acetate and 1 ml of methanol, followed by adding thereto 25 ml of a 1M solution of diphenyldiazomethane in ethyl acetate, and the resulting mixture was stirred at room temperature for 1 hour. The solvent was distilled off under reduced pressure and the resulting residue was purified by a silica gel column chromatography (eluent; chloroform: methanol=10:1) to obtain 6.8 g of diphenylmethyl (2,3-dioxopiperazin-1-yl)acetate as a white foamy substance.

IR (KBr) cm$^{-1}$: $v_{C=O}$ 1745, 1670.

NMR (d$_6$-DMSO) δ values: 3.2–3.8 (4H, m), 4.39 (2H, s), 6.85 (1H, s), 7.2–7.8 (10H, m), 8.67 (1H, brs).

Reference Example 21

Diphenylmethyl [4-[3-(tert-butoxycarbonyl-amino) propyl]-2,3-dioxopiperazin-1-yl]acetate In the same manner as in Reference Example 10, 0.68 g of diphenylmethyl [4-[3-(tert-butoxycarbonyl-amino) propyl]-2,3-dioxopiperazin-1-yl]acetate was obtained as a colorless oil from 1.0 g of diphenylmethyl (2,3-dioxopiperazin-1-yl)acetate and 0.77 g of 1-bromo-3-tert-butoxycarbonylpropane.

IR (neat) cm$^{-1}$: $v_{C=O}$ 1745, 1680.

NMR (CDCl$_3$) δ values: 1.42 (9H, s), 1.5–2.1 (2H, m), 3.0–3.7 (8H, m), 4.35 (2H, s), 6.90 (1H, s), 7.3–7.5 (10H, m), 8.00 (1H, brs).

Reference Example 22

Diphenylmethyl [4-(3-aminopropyl)-2,3-dioxopiperazin-1-yl]acetate hydrochloride

In 3 ml of ethyl acetate was dissolved 0.50 g of diphenylmethyl [4-[3-(tert-butoxycarbonylamino)-propyl]-2,3-dioxopiperazin-1-yl]acetate, followed by adding thereto 3.3 ml of a 1.5N solution of hydrochloric acid in dioxane, and the resulting mixture was stirred at room temperature for 3 hours. After completion of the reaction, the solvent was distilled off under reduced pressure to obtain 0.43 g of diphenylmethyl [4-(3-aminopropyl)-2,3-dioxopiperazin-1-yl]acetate hydrochloride as a yellow oil.

IR (neat) cm$^{-1}$: $v_{C=O}$ 1745, 1665.

Reference Example 23

Diphenylmethyl [4-[3-(4-cyanobenzenesulfonyl-amino)propyl]-2,3-dioxopiperazin-1-yl]acetate In 7 ml of tetrahydrofuran was dissolved 0.70 g of diphenylmethyl [4-(3-aminopropyl)-2,3-dioxopiperazin-1-yl]acetate hydrochloride, and 0.36 g of 4-cyanobenzenesulfonyl chloride and then 0.58 ml of triethylamine were added thereto under ice-cooling. After stirring at room temperature for 30 minutes, the reaction mixture was added to a mixed solvent of 20 ml of ethyl acetate and 20 ml of water and the pH was adjusted to 3 with 2N hydrochloric acid. The organic layer was separated, washed with water and then a saturated aqueous sodium chloride solution, and then dried over anhydrous magnesium sulfate. The solvent was distilled off under reduced pressure and the resulting residue was purified by a silica gel column chromatography (eluent; chloroform : methanol=20:1) to obtain 0.43 g of diphenylmethyl [4-[3-(4-cyanobenzenesulfonyl-amino)propyl]-2,3-dioxopiperazin-1-yl]acetate as a yellow foamy substance.

IR (KBr) cm$^{-1}$: $v_{C=O}$ 1750, 1675.

NMR (CDCl$_3$) δ values: 1.6–2.1 (2H, m), 2.6–3.2 (2H, m), 3.3–4.1 (6H, m), 4.31 (2H, s), 6.3–6.7 (1H, m), 6.89 (1H, s), 7.1–8.2 (14H, m).

Reference Example 24

Ethyl 4-[4-(2,4-dimethoxybenzyl)-2,3-dioxopiperazin-1-yl]butyrate 1-(2,4-Dimethoxybenzyl)-2,3-dioxopiperazine was reacted with ethyl 4-bromobutyrate by the same method as in Reference Example 12 to obtain ethyl 4-[4-(2,4-dimethoxybenzyl)-2,3-dioxopiperazin-1-yl]butyrate as an oil.

IR (KBr) cm$^{-1}$: $v_{C=O}$ 1730, 1670.

NMR (CDCl$_3$) δ values: 1.24 (3H, t, J=7 Hz), 1.7–3.1 (4H, m), 3.3–4.0 (12H, m), 4.12 (2H, q, J=7 Hz), 4.62 (2H, s), 6.3–6.6 (2H, m), 7.1–7.4 (1H, m).

Reference Example 25

Ethyl 4-(2,3-dioxopiperazin-1-yl)butyrate

Ethyl 4-(2,3-dioxopiperazin-1-yl)butyrate was obtained as an oil from ethyl 4-[4-(2,4-dimethoxy-benzyl)-2,3-dioxopiperazin-1-yl]butyrate by the same process as in Reference Example 14.

IR (neat) cm$^{-1}$: $v_{C=O}$ 1735, 1655.

NMR (CDCl$_3$) δ values: 1.24 (3H, t, J=8 Hz), 1.6–2.7 (4H, m), 3.3–3.9 (6H, m), 4.12 (2H, q, J=8 Hz), 8.66 (1H, brs).

Reference Example 26

Diphenylmethyl 4-(2,3-dioxopiperazin-1-yl)-butyrate

In 5 ml of ethanol was dissolved 0.50 g of ethyl 4-(2,3-dioxopiperazin-1-yl)butyrate, followed by adding thereto 2.2 ml of a 1N aqueous sodium hydroxide solution, and the resulting mixture was stirred at room temperature for 1 hour. Then, 0.2 ml of concentrated hydrochloric acid was added thereto and the solvent was distilled off under reduced pressure. To the resulting residue were added 4 ml of ethyl acetate, 1 ml of methanol and 2.4 ml of a 1M solution of diphenyldiazo-methane in ethyl acetate, and the resulting mixture was stirred at room temperature for 1 hour. The solvent was distilled off under reduced pressure and the resulting residue was purified by a silica gel column chromatography (eluent; chloroform : methanol =20:1) to obtain 0.61 g of diphenylmethyl 4-(2,3-dioxopiperazin-1-yl)-butyrate as a light-yellow oil.

IR (neat) cm$^{-1}$: $v_{C=O}$ 1720, 1685.

NMR (d$_6$-DMSO) δ values: 1.5–2.2 (2H, m), 2.3–2.7 (2H, m), 3.1–4.0 (6H, m), 6.80 (1H, s), 7.1–7.9 (10H, m), 8.51 (1H, brs).

Reference Example 27

Diphenylmethyl 4-(4-tert-butoxycarbonylmethyl-2,3-dioxopiperazin-1-yl)butyrate

With 1.30 g of diphenylmethyl 4-(2,3-dioxopiperazin-1-yl)butyrate was reacted 0.63 ml of tert-butyl bromoacetate by the same method as in Reference Example 12 to obtain 1.48 g of diphenylmethyl 4-(4-tert-butoxycarbonylmethyl-2,3-dioxopiperazin-1-yl)butyrate as a yellow oil.

IR (neat) cm$^{-1}$: $v_{C=O}$ 1730, 1680.

NMR (CDCl$_3$) δ values: 1.45 (9H, s), 1.8–2.7 (4H, m), 3.3–3.7 (6H, m), 4.08 (2H, s), 6.85 (1H, s), 7.0–7.4 (10H, m).

Reference Example 28

4-(4-tert-Butoxycarbonylmethyl-2,3-dioxopiperazin-1-yl)butyric acid

By the same process as in Reference Example 16, 0.62 g of 4-(4-tert-butoxycarbonylmethyl-2,3-dioxopiperazin-1-yl) butyric acid was obtained as colorless crystals from 1.30 g of diphenylmethyl 4-(4-tert -butoxycarbonylmethyl-2,3-dioxopiperazin-1-yl)-butyrate.

IR (KBr) cm$^{-1}$: $v_{C=O}$ 1715, 1665.

Example 1

Methyl [4-[3-(4-benzyloxycarbonylamidino-phenoxy)propyl]-2,3-dioxopiperazin-1-yl]acetate A mixture of 1.2 g of methyl (2,3-dioxopiperazin-1-yl) acetate, 0.26 g of sodium hydride (60%, oil) and 12 ml of N,N-dimethylformamide was stirred at room temperature for 30 minutes. Then, 2.52 g of 1-bromo-3-(4-benzyloxycarbonylamidinophenoxy)propane was added thereto and the resulting mixture was stirred at 60° C. for 2 hours. The reaction mixture was cooled and then added to a mixed solvent of 40 ml of ethyl acetate and 40 ml of water. After the pH was adjusted to 1 with 2N hydrochloric acid, the aqueous layer was separated. To the aqueous layer was added 40 ml of ethyl acetate and the pH was adjusted to 10 with potassium carbonate. The organic layer was separated and the aqueous layer was extracted with three 20-ml portions of ethyl acetate. The combined organic layer was washed with water and then a saturated aqueous sodium chloride solution and dried over anhydrous magnesium sulfate. The solvent was distilled off under reduced pressure and the resulting residue was purified by a silica gel column chromatography (eluent; chloroform: methanol =30:1) to obtain 1.17 g of methyl [4-[3-(4-benzyloxy-carbonylamidinophenoxy) propyl]-2,3-dioxopiperazin-1-yl] acetate as a colorless oil.

IR (KBr) cm$^{-1}$: $v_{C=O}$ 1745, 1675.

NMR (CDCl$_3$) δ values: 1.7–2.3 (2H, m), 3.2–4.3 (13H, m), 5.18 (2H, s), 6.82 (2H, d, J=9 Hz), 7.1–7.5 (5H, m), 7.6–9.3 (4H, m).

Examples 2 to 8

The compounds listed in Table 2 were obtained in the same manner as in Example 1.

TABLE 2

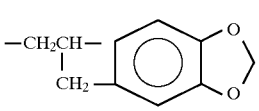

| Example No. | Y | A | R$^{2a}$ |
|---|---|---|---|
| 2 | $+CH_2+_2$ | $-CH_2-$ | $-CH_3$ |
| 3 | $+CH_2+_4$ | $-CH_2-$ | $-CH_3$ |
| 4 | $+CH_2+_5$ | $-CH_2-$ | $-CH_3$ |
| 5 | $+CH_2+_2$ | $-CH_2CH_2-$ | $-CH_3$ |
| 6 | $+CH_2+_3$ | $-CH_2CH_2-$ | $-CH_3$ |
| 7 | $+CH_2+_2$ | $-CH_2CH_2CH_2-$ | $-CH_2CH_3$ |
| 8 | $+CH_2+_3$ | 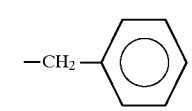 | $-CH_2-\phi$ |

Physical properties of the compounds listed in Table 2 are shown below.
No. 2
IR(KBr) cm$^{-1}$: $v_{c=o}$ 1750, 1685, 1655.
NMR(CDCl$_3$) δ values: 3.4–3.9(9H, m), 4.0–4.3(4H, m), 5.2(2H, s), 6.84(2H, d, J=9Hz), 7.1–7.5(5H, m), 7.85(2H, d, J=9Hz), 8.10(2H, brs).
No. 3
IR(neat) cm$^{-1}$: $v_{c=o}$ 1750, 1670.
NMR(CDCl$_3$) δ values: 1.5–1.9(4H, m), 3.4–4.2(13H, m), 5.18(2H, s), 6.83(2H, d, J=9Hz), 7.0–9.6(9H, m).
No. 4
IR(neat) cm$^{-1}$: $v_{c=o}$ 1745, 1660.
NMR(CDCl$_3$) δ values: 0.9–2.2(6H, m), 3.2–4.7(13H, m), 5.0–5.9(2H, m), 6.85(2H, d, J=9Hz), 7.1–8.5(9H, m).
No. 5

TABLE 2-continued

[Structure: CbzHN-C(=NH)-C6H4-O-Y-N(ring with two C=O)-N-A-COOR^{2a}]

| Example No. | Y | A | R^{2a} |
|---|---|---|---|

IR(KBr) cm$^{-1}$: $v_{c=o}$ 1740, 1665.
NMR(CDCl$_3$) δ values: 2.68(2H, t, J=6Hz), 3.4–4.4(13H, m), 5.25(2H, s), 6.87(2H, d, J=9Hz), 7.2–7.6(5H, m), 7.6–8.9(4H, m).
No. 6
IR(KBr) cm$^{-1}$: $v_{c=o}$ 1740, 1670.
NMR(CDCl$_3$) δ values: 1.9–2.3(2H, m), 2.65(2H, t, J=7Hz), 3.5–4.2(13H, m), 5.19(2H, s), 6.82(2H, d, J=9Hz), 7.2–9.3(9H, m).
No. 7
IR(KBr) cm$^{-1}$: $v_{c=o}$ 1735, 1665.
NMR(d$_6$-DMSO) δ values: 1.16(3H, t, 7Hz), 1.5–2.1(2H, m), 2.1–2.6(2H, m), 3.2–4.4(12H, m), 5.12(2H, s), 7.04(2H, d, J=9Hz), 7.40(5H, s), 8.03(2H, d, J=9Hz), 9.11(2H, brs).
No. 8
IR(neat) cm$^{-1}$: $v_{c=o}$ 1730, 1675.
NMR(CDCl$_3$) δ values: 1.8–2.4(2H, m), 2.6–4.4(13H, m), 4.9–5.5(4H, m), 5.87(2H, s), 6.4–7.0 (5H, m), 7.1–8.8(14H, m).

Example 9

The following compound was obtained in the same manner as in Example 1.

Methyl [4-[3-(4-benzyloxycarbonylamidinophenoxy)-propyl]-1,2,3,4-tetrahydro-2,3-dioxopyrazin-1-yl]acetate
IR (KBr) cm$^{-1}$: $v_{C=O}$ 1755, 1690, 1650.
NMR (d$_6$-DMSO) δ values: 1.9–2.6 (2H, m), 3.6–4.3 (7H, m), 4.56 (2H, s), 5.11 (2H, s), 6.60 (2H, s), 6.99 (2H, d, J=9 Hz), 7.37 (5H, s), 7.99 (2H, d, J=9 Hz), 9.60 (2H, brs).

Example 10

[4-[3-(4-Amidinophenoxy)propyl]-2,3-dioxopiperazin-1yl]acetic acid hydrochloride A mixture of 1.05 g of methyl [4-[3-(4-benzyloxycarbonylamidinophenoxy) propyl]-2,3-dioxopiperazin-1yl]acetate, 0.35 g of 5% palladium-carbon, 0.39 ml of 6N hydrochloric acid and 15 ml of methanol was subjected to hydrogenation at ordinary temperature and atmospheric pressure for 3 hours. Then, the pallasium-carbon was filtered off and the solvent was distilled off under reduced pressure to obtain 0.8 g of methyl [4-[3-(4-amidinophenoxy)propyl]-2,3-dioxopiperazin-1yl]acetate hydrochloride. The compound obtained was dissolved in 14 ml of 6N hydrochloric acid and the resulting solution was refluxed for 1 hour, after which the solvent was distilled off under reduced pressure to obtain 0.6 g of [4-[3-(4-amidinophenoxy)-propyl]- 2,3-dioxopiperazin-1-yl]acetic acid hydro-chloride as colorless crystals.

IR (KBr) cm$^{-1}$: $v_{C=O}$ 1740, 1670.

NMR (D$_2$O) δ values: 2.0–2.6 (2H, m), 3.2–3.8 (6H, m), 4.05 (2H, s), 4.32 (2H, t, J=6 Hz), 7.20 (2H, d, J=9 Hz), 7.83 (2H, d, J=9 Hz).

Examples 11 to 16

The compounds listed in Table 3 were obtained in the same manner as in Example 10.

TABLE 3

[Structure: H$_2$N-C(=NH)-C$_6$H$_4$-O-Y-N(ring with two C=O)-N-A-COOH]

| Example No. | Y | A |
|---|---|---|
| 11 | $(CH_2)_2$ | $-CH_2-$ |
| 12 | $(CH_2)_4$ | $-CH_2-$ |
| 13 | $(CH_2)_5$ | $-CH_2-$ |
| 14 | $(CH_2)_2$ | $-CH_2CH_2-$ |
| 15 | $(CH_2)_3$ | $-CH_2CH_2-$ |
| 16 | $(CH_2)_2$ | $-CH_2CH_2CH_2-$ |

Physical properties of the compounds listed in Table 3 are shown below.
No. 11
IR(KBr) cm$^{-1}$: $v_{c=o}$ 1735, 1685.
NMR(d$_1$-TFA) δ values: 3.7–4.2(6H, m), 4.3–4.7(4H, m) 7.14(2H, d, J=8.5 Hz), 7.82(2H, d, J=8.5Hz).
No. 12
IR(KBr) cm$^{-1}$: $v_{c=o}$ 1750, 1675.
NMR(D$_2$O) δ values: 1.6–2.3(4H, m), 3.0–4.5(10H, m), 7.18(2H, d, J=9Hz), 7.82(2H, d, J=9Hz).
No. 13
IR(KBr) cm$^{-1}$: $v_{c=o}$ 1735, 1670.
NMR(d$_6$-DMSO) δ values: 0.9–2.0(6H, m), 3.2–4.3(10H, m), 7.14(2H, d, J=9Hz), 7.89(2H, d, J=9Hz), 8.9–9.5 (5H, m).
No. 14
IR(KBr) cm$^{-1}$: $v_{c=o}$ 1720, 1685.
NMR(d$_1$-TFA) δ values: 3.18(2H, t, J=6Hz), 3.5–4.8(10H, m), 7.27(2H, d, J=9Hz), 7.90(2H, d, J=9Hz).
No. 15
IR(KBr) cm$^{-1}$: $v_{c=o}$ 1725, 1680.
NMR(d$_6$-DMSO) δ values: 1.8–4.5(14H, m), 7.37(2H, d, J=9Hz), 7.89(2H, d, J=9Hz), 8.7–10.8(5H, m).
No. 16
IR(KBr) cm$^{-1}$: $v_{c=o}$ 1685, 1665.
NMR(D$_2$O) δ values: 1.6–2.8(4H, m), 3.2–5.0(10H, m), 7.22(2H, d, J=9Hz), 7.72(2H, d, J=9Hz).

Example 17

The following compound was obtained in the same manner as in Example 10.

[4-[3-(4-Amidinophenoxy)propyl]-1,2,3,4-tetrahydro-2,3-dioxopyrazin-1-yl]acetic acid hydrochloride IR (KBr) cm$^{-1}$: $v_{C=O}$ 1720, 1685.

NMR (d$_6$-DMSO) δ values: 1.7–2.4 (2H, m), 3.1–4.6 (6H, m), 6.60 (2H, s), 7.08 (2H, d, J=9 Hz), 7.87 (2H, d, J=9 Hz), 8.6–9.5 (5H, m).

Example 18

Diphenylmethyl α-[4-[4-(4-benzyloxycarbonyl-amidinophenoxy) butyl]-2,3-dioxopiperazin-1-yl]-α-phenylacetate In 5 ml of N,N-dimethylformamide was dissolved 0.2 g of 1-[4-(4-benzyloxycarbonylamidinophenoxy)butyl]-2,3-dioxopiperazine, followed by adding thereto 20 mg of sodium hydride (60%, oil), and the resulting mixture was stirred at 50° C. for 30 minutes. The reaction mixture was cooled to room temperature and 0.17 g of diphenyl-methyl α-bromophenylacetate was added thereto. After stirring at the same temperature for 2 hours, the reaction mixture was added to a mixed solvent of 20 ml of ethyl acetate and 20 ml of water. The organic layer as separated, washed with water and then a saturated aqueous sodium chloride solution, and then dried over anhydrous magnesium sulfate. The solvent was distilled off under reduced pressure and the resulting residue was purified by a silica gel column chromatography (eluent; chloroform: methanol=20:1) to obtain 0.29 g of diphenylmethyl α-[4-[4-(4-benzyloxycarbonylamidinophenoxy) butyl]-2,3-dioxopiperazin-1-yl]-α-phenylacetate as a colorless oil.

IR (KBr) cm$^{-1}$: $v_{C=O}$ 1745, 1675.

NMR (CDCl$_3$) δ values: 1.4–1.9 (4H, m), 2.9–4.1 (8H, m), 5.18 (2H, s), 6.60 (1H s), 6.7–8.5 (27H, m).

Example 19

α-[4-[4-(4-Amidinophenoxy)butyl]-2,3-dioxopiperazin-1yl]-α-phenylacetic acid

A mixture of 0.25 g of diphenylmethyl α-[4-[4-(4-benzyloxycarbonylamidinophenoxy)butyl]-2,3-dioxopiperazin-1-yl]-α-phenylacetate, 0.13 g of 5% palladium-carbon, 0.34 ml of 1N hydrochloric acid and 5 ml of N,N-dimethylformamide was subjected to hydrogenation at ordinary temperature and atmospheric pressure for 3 hours. Then, the pallasium-carbon was filtered off and the filtrate was concentrated under reduced pressure. To the resulting residue were added 2 ml of ethyl acetate, 5 ml of water and 30 mg of sodium hydrogencarbonate to dissolve the residue. The aqueous layer was separated and then purified by a reversed phase column chromatography (eluent: a 50% aqueous acetonitrile solution) to obtain 0.10 g of α-[4-[4-(4-amidinophenoxy)butyl]-2,3-dioxopiperazin-1-yl]-α-phenylacetic acid as colorless crystals.

IR (KBr) cm$^{-1}$: $v_{C=O}$ 1665.

NMR (d$_1$-TFA) δ values: 1.8–2.2 (4H, m), 3.2–4.4 (8H, m), 6.49 (1H s), 7.14 (2H, d, J=9 Hz), 7.3–7.7 (5H, m), 7.79 (2H, d, J=9 Hz).

Example 20

The following compound was obtained in the same manner as in Example 19.

2-[(1,3-Benzodioxol-5-yl)methyl]-3-[4-[3-(4-amidinophenoxy) propyl]-2,3-dioxopiperazin-1-yl] propionic acid IR (KBr) cm$^{-1}$: $v_{C=O}$ 1655.

NMR (d$_1$-TFA) δ values: 1.9–2.5 (2H, m), 2.7–4.4 (13H, m), 5.97 (2H, s), 6.5–7.4 (5H, m), 7.79 (2H, d, J=9 Hz).

Example 21

Diphenylmethyl 3-[4-[3-(4-tert-butoxycarbonyl-amidinophenoxy)propyl]-2,3-dioxopiperazin-1-yl]-3-(pyridin-3-yl) propionate In 7.5 ml of N,N-dimethylformamide was dissolved 2.5 g of 4-[3-(4-tert-butoxycarbonylamidinophenoxy) propyl]-2,3-dioxopiperazine, and to the solution were added 6.1 g of diphenylmethyl 3-(3-pyridyl)acrylate and 0.48 ml of 1,8-diazabicyclo[5.4.0]undec-7-ene. The resulting mixture was stirred overnight at room temperature and distilled under reduced pressure to remove the solvent. To the resulting residue were added 80 ml of ethyl acetate and 60 ml of water and the pH was adjusted to 7 with 2N hydrochloric acid. The organic layer was separated, washed with water and then a saturated aqueous sodium chloride solution, and then distilled under reduced pressure to remove the solvent. The resulting residue was purified by a silica gel column chromatography (eluent; chloroform: methanol=20:1) to obtain 2.34 g of diphenylmethyl 3-[4-[3-(4-tert-butoxycarbonylamidinophenoxy)propyl]-2,3-dioxopiperazin-1-yl]-3-(pyridin-3-yl)propionate as a colorless oil.

IR (KBr) cm$^{-1}$: $v_{C=O}$ 1735, 1675.

NMR (CDCl$_3$) δ values: 1.52 (9H, s), 1.7–2.6 (4H, m), 2.8–4.2 (8H, m), 5.7–6.1 (1H, m), 6.7–6.9 (3H, m), 7.0–9.2 (18H, m).

Examples 22 to 51

The compounds listed in Table 4, Table 5, Table 6 and Table 7 were obtained in the same manner as in Example 21.

TABLE 4

| Example No. | R | Y | A | R$^{2a}$ |
|---|---|---|---|---|
| 22 | Boc | ⁺CH$_2$⁺$_3$ |  | DPM |
| 23 | Boc | ⁺CH$_2$⁺$_3$ |  | DPM |
| 24 | Boc | ⁺CH$_2$⁺$_3$ | (thiophene) | DPM |

TABLE 4-continued

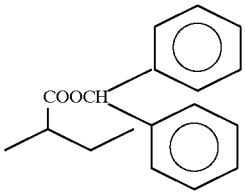

| Example No. | R | Y | A | R2a |
|---|---|---|---|---|
| 25 | Boc | $(CH_2)_3$ | (2-methyl-3,3-diphenylpropanoate-CH group) | DPM |
| 26 | Boc | $(CH_2)_3$ | (N-methyl-N-benzyl-2-methylbutanamide group) | DPM |
| 27 | Boc | $(CH_2)_3$ | (4-methoxyphenyl sec-butyl) | DPM |
| 28 | Boc | $(CH_2)_3$ | (4-fluorophenyl sec-butyl) | DPM |
| 29 | Boc | $(CH_2)_3$ | (benzodioxole sec-butyl) | DPM |
| 30 | Boc | $(CH_2)_3$ | (furan-2-yl sec-butyl) | DPM |

TABLE 5

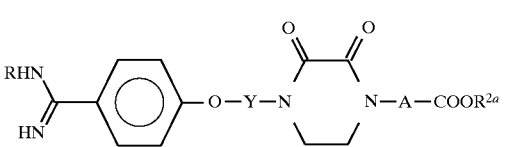

| Example No. | R | Y | A | R2a |
|---|---|---|---|---|
| 31 | Boc | $(CH_2)_3$ | (2,4-difluorophenyl sec-butyl) | DPM |
| 32 | Boc | $(CH_2)_3$ | (3-methoxyphenyl sec-butyl) | DPM |
| 33 | Cbz | $(CH_2)_4$ | (pyridin-3-yl sec-butyl) | DPM |
| 34 | Boc | $(CH_2)_3$ | (pyridin-4-yl sec-butyl) | DPM |
| 35 | Boc | $(CH_2)_3$ | (pyridin-2-yl sec-butyl) | DPM |
| 36 | Boc | $(CH_2)_3$ | (3-ethylhexyl) | DPM |
| 37 | Boc | $(CH_2)_3$ | (cyclopropyl sec-butyl) | DPM |
| 38 | Boc | $(CH_2)_3$ | (naphthalen-2-yl sec-butyl) | DPM |

TABLE 5-continued

RHN-C(=NH)-C6H4-O-Y-N(-CH2CH2CH2-)N-A-COOR²ᵃ with two C=O between the two N

| Example No. | R | Y | A | R²ᵃ |
|---|---|---|---|---|
| 39 | Boc | ⁺(CH₂)₃ | (1-sec-butyl-naphthalen-4-yl) | DPM |

TABLE 6

RHN-C(=NH)-C6H4-O-Y-N(-CH2CH2CH2-)N-A-COO²ᵃ

| Example No. | R | Y | A | R²ᵃ |
|---|---|---|---|---|
| 40 | Boc | ⁺(CH₂)₃ | benzothiophen-S-yl with sec-butyl | DPM |
| 41 | Boc | ⁺(CH₂)₃ | (sec-butyl)phenyl | DPM |
| 42 | Boc | ⁺(CH₂)₃ | (sec-butyl)pyridinyl | Et |

TABLE 7

RHN-C(=NH)-C6H4-O-Y-N(-CH2CH2CH2-)N-A-COOR²ᵃ

| Example No. | R | Y | A | R²ᵃ |
|---|---|---|---|---|
| 43 | Boc | ⁺(CH₂)₃ | 3-F, sec-butyl phenyl | DPM |

TABLE 7-continued

RHN-C(=NH)-C6H4-O-Y-N(-CH2CH2CH2-)N-A-COOR²ᵃ

| Example No. | R | Y | A | R²ᵃ |
|---|---|---|---|---|
| 44 | Boc | ⁺(CH₂)₃ | thiophene with sec-butyl | DPM |
| 45 | Boc | ⁺(CH₂)₃ | 2-CH₃-pyridinyl with sec-butyl | DPM |
| 46 | Boc | ⁺(CH₂)₃ | 3-SO₂CH₃-phenyl with sec-butyl | DPM |
| 47 | Boc | ⁺(CH₂)₃ | 2-F-phenyl with sec-butyl | DPM |
| 48 | Boc | ⁺(CH₂)₃ | 2-CH₃-phenyl with sec-butyl | DPM |
| 49 | Boc | ⁺(CH₂)₃ | 3-CH₃-phenyl with sec-butyl | DPM |
| 50 | Boc | ⁺(CH₂)₃ | 2-OCH₃-phenyl with sec-butyl | DPM |
| 51 | Boc | ⁺(CH₂)₃ | pyrazine with sec-butyl | Et |

Physical properties of the compounds listed in Table 4, Table 5, Table 6 and Table 7 are shown below.
No. 22

TABLE 7-continued

RHN-C(=NH)-[phenyl]-O-Y-N[2,3-dioxopiperazine]N-A-COOR²ᵃ

| Example No. | R | Y | A | R²ᵃ |
|---|---|---|---|---|

IR(KBr) cm⁻¹: $\nu_{C=O}$ 1735, 1675.
NMR(CDCl₃) δ values: 1.26(3H, d, J=6.5Hz), 1.54(9H, s), 1.9–2.2(2H, m), 2.7–3.0(2H, m), 3.1–3.7(2H, m), 3.97(2H, t, J=6Hz), 4.5–5.1(1H, m), 6.80 (1H, s), 6.85(2H, d, J=8.5Hz), 7.2–7.5(10H, m), 7.7–8.2(4H, m).
No. 23
IR(KBr) cm⁻¹: $\nu_{C=O}$ 1735, 1670.
NMR(CDCl₃) δ values: 1.55(9H, s), 1.8–2.2(2H, m), 2.9–3.7(8H, m), 3.8–4.1 (2H, m), 6.0–6.4(1H, m), 6.7–7.0(3H, m), 7.2–8.2(19H, m).
No. 24
IR(KBr) cm⁻¹: $\nu_{C=O}$ 1735, 1685.
NMR(CDCl₃) δ values: 1.55(9H, s), 1.9–2.2(2H, m), 2.8–3.7(8H, m), 3.98 (2H, t, J=6Hz), 6.1–6.5(1H, m), 6.7–7.0(3H, m), 7.2–7.4(13H, m), 7.6–8.1 (4H, m).
No. 25
IR(KBr) cm⁻¹: $\nu_{C=O}$ 1735, 1685.
NMR(CDCl₃) δ values: 1.55(9H, s), 1.8–2.2(2H, m), 3.0–4.4(10H, m), 4.9–5.3(1H, m), 6.6–7.0(4H, m), 7.0–9.0(24H, m).
No. 26
IR(KBr) cm⁻¹: $\nu_{C=O}$ 1740, 1675, 1660.
NMR(CDCl₃) δ values: 1.53(9H, s), 1.7–2.6(4H, m), 2.7–4.2(11H, m), 4.2–4.9(2H, m), 5.7–6.2(1H, m), 6.84(1H, s), 6.85(2H, d, J=8Hz), 7.0–8.8 (19H, m).
No. 27
IR(KBr) cm⁻¹: $\nu_{C=O}$ 1735, 1675.
NMR(CDCl₃) δ values: 1.55(9H, s), 1.8–2.2(2H, m), 2.8–3.7(8H, m), 3.79 (3H, s), 3.96(2H, t, J=6Hz), 6.10(1H, m), 6.7–6.9(5H, m), 7.1–8.2(14H, m).
No. 28
IR(KBr) cm⁻¹: $\nu_{C=O}$ 1740, 1675.
NMR(d₆-DMSO) δ values: 1.46(9H, s), 1.7–2.1(2H, m), 3.2–3.8(8H, m), 3.8–4.3(2H, m), 5.8–6.2(1H, m), 6.7–8.4(19H, m), 9.0(2H, bs).
No. 29
IR(KBr) cm⁻¹: $\nu_{C=O}$ 1735, 1675.
NMR(CDCl₃) δ values: 1.52(9H, s), 1.7–2.3(2H, m), 2.8–4.2(10H, m), 5.8–6.2(3H, m), 6.6–7.0(6H, m), 7.1–8.3(14H, m).
No. 30
IR(neat) cm⁻¹: $\nu_{C=O}$ 1735, 1685, 1675.
NMR(CDCl₃) δ values: 1.55(9H, s), 1.8–2.2(2H, m), 2.8–3.8(10H, m), 3.8–4.2(2H, m), 6.0–6.3(1H, m), 6.7–8.1(17H, m), 13.5(2H, bs).
No. 31
IR(KBr) cm⁻¹: $\nu_{C=O}$ 1735, 1675.
NMR(CDCl₃) δ values: 1.55(9H, s), 1.8–2.2(2H, m), 3.1–4.2(10H, m), 5.4–5.8(1H, m), 6.6–9.0(20H, m).
No. 32
IR(KBr) cm⁻¹: $\nu_{C=O}$ 1735, 1675.
NMR(CDCl₃) δ values: 1.55(9H, s), 1.8–2.3(2H, m), 2.9–4.1(13H, m), 6.0–6.3(1H, m), 6.7–7.7(17H, m), 7.8–8.8(4H, m).
No. 33
IR(KBr) cm⁻¹: $\nu_{C=O}$ 1735, 1670.
NMR(CDCl₃) δ values: 1.6–1.9(4H, m), 3.1–3.7(8H, m), 4.0–4.2(2H, m), 5.21(2H, s), 5.7–6.2(1H, m), 6.8–8.1(22H, m), 8.5–9.3(4H, m).
No. 34
IR(KBr) cm⁻¹: $\nu_{C=O}$ 1735, 1675.
NMR(d₆-DMSO) δ values: 1.45(9H, s), 1.7–2.2(2H, m), 3.1–4.2(10H, m), 5.6–6.1(1H, m), 6.8–8.7(19H, m), 9.00(2H, brs).
No. 35
IR(KBr) cm⁻¹: $\nu_{C=O}$ 1735, 1675.
NMR(d₆-DMSO) δ values: 1.45(9H, s), 1.7–2.3(2H, m), 2.8–4.3(10H, m), 5.8–6.2(1H, m), 6.78(1H, s), 6.96(2H, d, J=9Hz), 7.2–8.3(15H, m), 8.3–8.6 (1H, m), 8.8–9.1(2H, m).
No. 36
IR(KBr) cm⁻¹: $\nu_{C=O}$ 1740, 1675.
NMR(CDCl₃) δ values: 0.6–2.2(20H, m), 2.6–3.7(8H, m), 3.9–4.2(2H, m), 4.3–4.8(1H, m), 6.6–7.0(3H, m), 7.33(10H, s), 7.88(2H, d, J=9Hz), 8.20(2H, brs).
No. 37
IR(KBr) cm⁻¹: $\nu_{C=O}$ 1735, 1675.
NMR(CDCl₃) δ values: 0.2–0.7(4H, m), 0.9–1.4(1H, m), 1.55(9H, s), 1.8–2.4 (2H, m), 2.8–4.2(11H, m), 6.8–7.0(3H, m), 7.30(10H, s), 7.7–8.7(4H, m).
No. 38
IR(KBr) cm⁻¹: $\nu_{C=O}$ 1735, 1670
NMR(CDCl₃) δ values: 1.54(9H, s), 1.8–2.2(2H, m), 2.8–4.1(10H, m), 6.2–6.5(1H, m), 6.83(1H, s), 7.1–8.1(23H, m).
No. 39
IR(KBr) cm⁻¹: $\nu_{C=O}$ 1735, 1675.
NMR(CDCl₃) δ values: 1.54(9H, s), 1.7–2.2(2H, m), 2.8–4.1(10H, m), 6.6–8.3(24H, m).
No. 40
IR(KBr) cm⁻¹: $\nu_{C=O}$ 1735, 1675.
NMR(CDCl₃) δ values: 1.54(9H, s), 1.8–2.2(2H, m), 2.8–3.7(8H, m), 3.8–4.1 (2H, m), 6.1–6.4(1H, m), 6.6–6.9(3H, m), 7.1–7.6(14H, m), 7.6–8.1(5H, m).
No. 41
IR(KBr) cm⁻¹: $\nu_{C=O}$ 1735, 1675.
NMR(CDCl₃) δ values: 1.54(9H, s), 1.8–2.3(2H, m), 2.8–4.1(10H, m), 4.2–4.6(1H, m), 6.7–7.4(18H, m), 7.5–8.7(4H, m).
No. 42
IR(KBr) cm⁻¹: $\nu_{C=O}$ 1735, 1685.
NMR(CDCl₃) δ values: 1.23(3H, t, J=7Hz), 1.55(9H, s), 1.8–2.3(2H, m), 3.0–4.5(12H, m), 5.8–6.2(1H, m), 6.86(2H, d, J=9Hz), 7.2–8.3(6H, m), 8.5–8.7(2H, m).
No. 43
IR(KBr) cm⁻¹: $\nu_{C=O}$ 1735, 1675.
NMR(CDCl₃) δ values: 1.54(9H, s), 1.7–2.3(2H, m), 2.9–4.2(10H, m), 5.8–6.3(1H, m), 6.7–7.6(17H, m), 7.6–8.7(4H, m).
No. 44
IR(KBr) cm⁻¹: $\nu_{C=O}$ 1735, 1675.
NMR(CDCl₃) δ values: 1.54(9H, s), 1.8–2.3(2H, m), 2.8–4.2(10H, m), 5.9–6.3(1H, m), 6.6–7.4(16H, m), 7.6–8.5(4H, m).
No. 45
IR(KBr) cm⁻¹: $\nu_{C=O}$ 1735, 1675.
NMR(CDCl₃) δ values: 1.55(9H, s), 1.8–2.3(2H, m), 2.43(3H, s), 2.8–4.2 (10H, m), 5.9–6.2(1H, m), 6.6–8.2(19H, m), 8.3–8.6(1H, m).
No. 46
IR(KBr) cm⁻¹: $\nu_{C=O}$ 1735, 1675.
NMR(CDCl₃) δ values: 1.54(9H, s), 1.8–2.3(2H, m), 2.8–4.2(13H, m), 5.8–6.2(1H, m), 6.6–7.0(3H, m), 7.0–8.7(18H, m).
No. 47
IR(KBr) cm⁻¹: $\nu_{C=O}$ 1735, 1675.
No. 48
IR(KBr) cm⁻¹: $\nu_{C=O}$ 1735, 1675.
NMR(CDCl₃) δ values: 1.55(9H, s), 1.8–2.4(5H, m), 2.8–4.2(10H, m), 6.0–6.2(1H, m), 6.7–7.4(17H, m), 7.6–8.2(4H, m).
No. 49
IR(KBr) cm⁻¹: $\nu_{C=O}$ 1735, 1675.
NMR(CDCl₃) δ values: 1.53(9H, s), 1.7–2.4(5H, m), 2.7–4.1(10H, m), 5.9–6.3(1H, m), 6.6–7.6(17H, m), 7.6–8.8(4H, m).
No. 50
IR(KBr) cm⁻¹: $\nu_{C=O}$ 1735, 1675.
NMR(CDCl₃) δ values: 1.55(9H, s), 1.8–2.4(5H, m), 2.8–4.1(13H, m), 5.6–5.9(1H, m), 6.7–8.7(20H, m).
No. 51
IR(KBr) cm⁻¹: $\nu_{C=O}$ 1735, 1685.
NMR(CDCl₃) δ values: 1.0–2.4(14H, m), 2.9–4.4(12H, m), 5.6–6.0(1H, m), 6.84(2H, d, J=8.5Hz), 7.85(2H, d, J=8.5Hz), 8.4–9.3(5H, m).

Example 52

Ethyl 3-[4-[3-(4-cyanophenoxy)propyl]-2,3-dioxopiperazin-1-yl]-3-(pyridin-3-yl)propionate This compound was obtained in the same manner as in Example 21.

IR (KBr) cm⁻¹: $\nu_{CN}$ 2225, $\nu_{C=O}$ 1730, 1665.

NMR (CDCl₃) δ values: 1.22 (3H, t, J=7 Hz), 1.8–2.4 (2H, m), 2.8–4.4 (12H, m), 5.8–6.2 (1H, m), 6.90 (2H, d, J=9 Hz), 7.1–7.9 (4H, m), 8.4–8.7 (2H, m).

Example 53

3-[4-[3-(4-Cyanophenoxy)propyl]-2,3-dioxopiperazin-1-yl]-3-(pyridin-3-yl)propionic acid In 70 ml of 6N hydrochloric acid was dissolved 7.0 g of ethyl 3-[4-[3-(4-cyanophenoxy)propyl]-2,3-dioxopiperazin- 1-yl]-3-(pyridin-3-yl)propionate, and the solution was stirred at 50° C. for 1.5 hours and then cooled to room temperature. The reaction solution was adjusted to pH 4.0 with a 15% aqueous sodium hydroxide solution and the crystals precipitated were collected by filtration to obtain 4.6 g of 3-[4-[3-(4-cyanophenoxy)-propyl]-2,3-dioxopiperazin-1-yl]-3-(pyridin-3-yl)-propionic acid as colorless crystals.

IR (KBr) cm$^{-1}$: $v_{CN}$ 2225, $v_{C=O}$ 1670.

NMR (d$_6$-DMSO) δ values: 1.7–2.3 (2H, m), 2.9–3.8 (8H, m), 3.9–4.9 (3H, m), 5.6–6.1 (1H, m), 7.05 (2H, d, J=9 Hz), 7.3–7.6 (1H, m), 7.6–8.0 (3H, m), 8.4–8.7 (2H, m).

Example 54

(R)–(+)-1-Phenethylamine salt of (–)-3-[4-[3-(4-cyanophenoxy) propyl]-2,3-dioxopiperazin-1-yl]-3-(pyridin-3-yl) propionic acid In 15 ml of methanol was suspended 5 g of 3-[4-[3-(4-cyanophenoxy)propyl]-2,3-dioxopiperazin-1-yl]-3-(pyridin-3-yl)propionic acid, and 1.43 g of (R)–(+)-1-phenethylamine and 150 ml of acetonitrile were added thereto to obtain a homogeneous solution. The solution was allowed to stand overnight at room temperature, after which the crystals precipitated was collected by filtration to obtain 3.3 g of crude crystals of (R)–(+)-1-phenethylamine salt of (–)-3-[4-[3-(4-cyanophenoxy)-propyl]-2,3-dioxopiperazin-1-yl]-3-(pyridin-3-yl)-propionic acid. The crude crystals were recrystallized twice from a mixed solvent (methanol:acetonitrile=10:1) to obtain 1.14 g of colorless needles having a melting point of 156.5°–159.5° C. (decomp.).

IR (KBr) cm$^{-1}$: $v_{CN}$ 2220, $v_{C=O}$ 1685, 1660.

NMR (d$_6$-DMSO) δ values: 1.39 (3H, t, J=7 Hz), 1.8–2.2 (2H, m), 2.6–3.0 (2H, m), 3.3–3.8 (6H, m), 3.9–4.4 (3H, m), 5.30 (3H, brs), 5.7–6.0 (1H, m), 6.9–7.9 (11H, m), 8.3–8.7 (2H, m).

Example 55

(–)-3-[$^4$-[3-(4-Cyanophenoxy)propyl]-2,3-dioxopiperazin-1-yl]-3-(pyridin-3-yl)propionic acid In 10 ml of water was dissolved 1.0 g of (R)–(+)-1-phenethylamine salt of (–)-3-[4-[3-(4-cyano-phenoxy)propyl]-2,3-dioxopiperazin-1-yl]-3-(pyridin-3-yl) propionic acid, and 1.84 ml of 1N hydrochloric acid was added dropwise thereto at room temperature. The resulting mixture was stirred at the same temperature for 30 minutes, after which the crystals precipitated were collected by filtration to obtain 0.75 g of (–)-3-[4-[3-(4-cyanophenoxy)propyl]-2,3-dioxopiperazin-1-yl ]-3-(pyridin-3-yl)propionic acid as colorless crystals having a melting point of 199°–200° C.

IR (KBr) cm$^{-1}$: $v_{CN}$ 2225, $v_{C=O}$ 1670.

Example 56

Ethyl (–)-3-[4-[3-(4-cyanophenoxy)propyl]-2,3-dioxopiperazin-1-yl]-3-(pyridin-3-yl)propionate In 14 ml of ethanol was suspended 0.70 g of (–)-3-[4-[3-(4-cyanophenoxy)propyl]-2,3-dioxopiperazin-1 -yl]-3-(pyridin-3-yl)propionic acid, followed by adding thereto 0.15 ml of thionyl chloride under ice-cooling, and the resulting mixture was heated under reflux for 1 hour. After completion of the reaction, the solvent was distilled off under reduced pressure and 10 ml of ethyl acetate and 10 ml of water were added to the resulting residue, and the pH was adjusted to 7.5 with a saturated aqueous sodium hydrogencarbonate solution. The organic layer was separated and the aqueous layer was extracted three times with ethyl acetate. The combined organic layer was washed with a saturated aqueous sodium chloride solution and dried over anhydrous magnesium sulfate, after which the solvent was distilled off under reduced pressure to obtain 0.5 g of ethyl (–)-3-[4-[3-(4-cyanophenoxy) propyl]-2,3-dioxopiperazin-1-yl]-3-(pyridin-3-yl) propionate as colorless crystals having a melting point of 110.5°–112° C.

IR (KBr) cm$^{-1}$: $v_{CN}$ 2220, $v_{C=O}$ 1730, 1665.

Example 57

(–)-3-[4-[3-(4-Amidinophenoxy)propyl]-2,3-dioxopiperazin-1-yl ]-3-(pyridin-3-yl)propionic acid In 9 ml of ethanol was suspended 0.45 g of ethyl (–)-3-[4-[3-(4-cyanophenoxy)propyl]-2,3-dioxopiperazin-1-yl]-3-(pyridin-3-yl)propionate, and hydrogen chloride gas was introduced into the suspension under ice-cooling until the suspension was saturated therewith. The resulting solution was allowed to stand overnight at room temperature and then distilled under reduced pressure to remove the solvent. To the resulting residue were added 9 ml of ethanol and 1.2 ml of a 3N solution of ammonia in ethanol, and the resulting mixture was heated under reflux for 3 hours and then distilled under reduced pressure to remove the solvent. To the resulting residue was added 4.5 ml of 6N hydrochloric acid and the resulting mixture was stirred at 70° C. for 1 hour. The reaction mixture was cooled to room temperature and adjusted to pH 4.5 with sodium hydrogencarbonate. Purifying the pH-adjusted reaction mixture by a reversed phase column chromatography (eluent: 20% aqueous acetonitrile solution) gave 0.23 g of (–)-3-[4-[3-(4-amidinophenoxy)propyl]-2,3-dioxopiperazin-1-yl]-3-(pyridin-3-yl)propionic acid as colorless crystals having a melting point of 246°–248° C. (decomp.).

IR (KBr) cm$^{-1}$: $v_{C=O}$ 1665: $[\alpha]_d$=–91.7 (C=1.0, H$_2$O)

Example 58

3-[4-[3-(4-Amidinophenoxy)propyl]-2,3-dioxopiperazin-1-yl]-3-(pyridin-3-yl)propionic acid A mixture of 2.3 g of diphenylmethyl 3-[4-[3-(4-tert-butoxycarbonylamidinophenoxy) propyl]-2,3-dioxopiperazin-1-yl]-3-(pyridin-3-yl)propionate, 18.5 ml of anisole and 37 ml of trifluoroacetic acid was stirred at room temperature for 3 hours and then distilled under reduced pressure to remove the solvent. The resulting residue was suspended in a mixed solvent of 15 ml of ethyl acetate and 13 ml of water, followed by adding thereto 0.55 g of sodium hydrogencarbonate, and the resulting mixture was stirred at room temperature for 30 minutes. The aqueous layer was separated, adjusted to pH 3.5 with a saturated aqueous sodium hydrogencarbonate solution, and then concentrated to a volume of about 10 ml under reduced pressure. The resulting concentrate was purified by a reversed phase column chromatography (eluent: 25% aqueous acetonitrile solution) to obtain 0.82 g of 3-[4-[3-(4-amidinophenoxy) propyl]-2,3-dioxopiperazin- 1-yl]-3-(pyridin-3-yl)propionic acid as colorless crystals.

IR (KBr) cm$^{-1}$: $v_{C=O}$ 1670.

NMR (d$_1$-TFA) δ values: 2.0–2.5 (2H, m), 3.5–4.5 (10H, m), 5.7–6.1 (1H, m), 7.17 (2H, d, J=9 Hz), 7.85 (2H, d, J=9 Hz), 8.23 (1H, t, J=7 Hz), 8.8–9.1 (2H, m), 9.23 (1H, s).

Examples 59 to 87

The compounds listed in Table 8, Table 9, Table 10 and Table 11 were obtained in the same manner as in Example 58.

TABLE 8
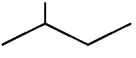
| Example No. | Y | A |
|---|---|---|
| 59 | $-(CH_2)_3-$ | 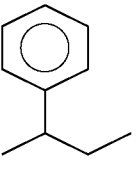 |
| 60 | $-(CH_2)_3-$ | 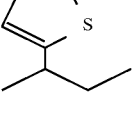 |
| 61 | $-(CH_2)_3-$ | 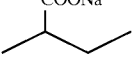 |
| 62 | $-(CH_2)_3-$ | 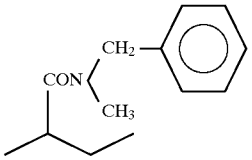 |
| 63 | $-(CH_2)_3-$ | 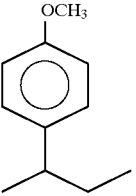 |
| 64 | $-(CH_2)_3-$ | 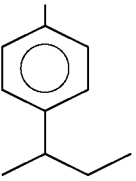 |
| 65 | $-(CH_2)_3-$ | 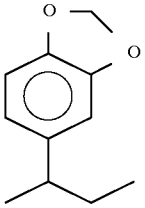 |
| 66 | $-(CH_2)_3-$ | 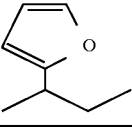 |
| 67 | $-(CH_2)_3-$ | 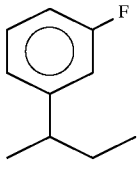 |
TABLE 9
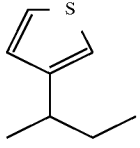
| Example No. | Y | A |
|---|---|---|
| 68 | $-(CH_2)_3-$ | 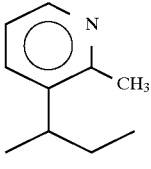 |
| 69 | $-(CH_2)_3-$ | 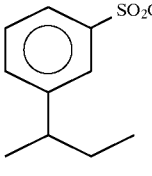 |
| 70 | $-(CH_2)_3-$ | 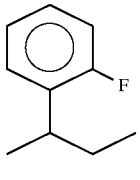 |
| 71 | $-(CH_2)_3-$ | 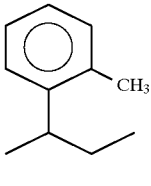 |
| 72 | $-(CH_2)_3-$ | 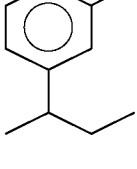 |
| 73 | $-(CH_2)_3-$ | 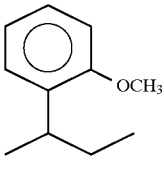 |
| 74 | $-(CH_2)_3-$ | |
| 75 | $-(CH_2)_3-$ | |

TABLE 9-continued

[Structure: H2N(HN)C-C6H4-O-Y-N(C(=O)C(=O))N-A-COOH with ring]

| Example No. | Y | A |
|---|---|---|
| 76* | ⁻(CH₂)₃⁻ | pyrazinyl with sec-butyl |

*In place of trifluoroacetic acid, 6N hydrochloric acid was used.

TABLE 10

[Structure: H2N(HN)C-C6H4-O-Y-N(C(=O)C(=O))N-A-COOH with ring]

| Example No. | Y | A |
|---|---|---|
| 77 | ⁻(CH₂)₃⁻ | 2,4-difluorophenyl with sec-butyl |
| 78 | ⁻(CH₂)₃⁻ | 3-methoxyphenyl with sec-butyl |
| 79 | ⁻(CH₂)₄⁻ | pyridyl with sec-butyl |
| 80 | ⁻(CH₂)₃⁻ | pyridyl with sec-butyl |
| 81 | ⁻(CH₂)₃⁻ | pyridyl with sec-butyl |

TABLE 10-continued

[Structure: H2N(HN)C-C6H4-O-Y-N(C(=O)C(=O))N-A-COOH with ring]

| Example No. | Y | A |
|---|---|---|
| 82 | ⁻(CH₂)₃⁻ | 2-ethylhexyl chain |
| 83 | ⁻(CH₂)₃⁻ | cyclopropyl with sec-butyl |
| 84 | ⁻(CH₂)₃⁻ | naphthyl with sec-butyl |
| 85 | ⁻(CH₂)₃⁻ | naphthyl with sec-butyl |

TABLE 11

[Structure: H2N(HN)C-C6H4-O-Y-N(C(=O)C(=O))N-A-COOH with ring]

| Example No. | Y | A |
|---|---|---|
| 86 | ⁻(CH₂)₃⁻ | benzothiophenyl with sec-butyl |
| 87 | ⁻(CH₂)₃⁻ | phenyl with sec-butyl |

Physical properties of the compounds listed in Table 8, Table 9, Table 10 and Table 11 are shown below.

TABLE 11-continued $$\text{H}_2\text{N}-\text{C}(=\text{NH})-\text{C}_6\text{H}_4-\text{O}-Y-N\underset{\underset{O}{\|}}{\overset{\overset{O}{\|}}{-\text{C}-\text{C}-}}N-A-\text{COOH}$$

| Example No. | Y | A |
|---|---|---|

No. 59
IR(KBr) cm$^{-1}$: $\nu_{c=o}$ 1680.
NMR (d$_1$-TFA): 1.47(3H, d, J=7Hz), 2.1–2.5(2H, m), 2.8–3.1(2H, m), 3.7–4.1(6H, m), 4.1–4.4(2H, m), 4.7–5.3(1H, m), 7.13(2H, d, J=9Hz), 7.80 (2H, d, J=9Hz).
No. 60
IR(KBr) cm$^{-1}$: $\nu_{c=o}$ 1665.
NMR(d$_1$-TFA): 2.1–2.4(2H, m), 3.36(2H, d, J=8Hz), 3.7–4.4(8H, m), 6.29 (1H, t, J=8Hz), 7.12(2H, d, J=8Hz), 7.48(5H, s), 7.83(2H, d, J=8Hz).
No. 61
IR(KBr) cm$^{-1}$: $\nu_{c=o}$ 1670.
NMR(d$_1$-TFA): 2.0–2.6(2H, m), 3.38(2H, d, J=7.5Hz), 3.7–4.0(6H, m), 4.1–4.4(2H, m), 6.43(1H, t, J=7.5Hz), 7.0–7.3(4H, m), 7.4–7.5(1H, m), 7.80(2H, d, J=8Hz).
No. 62
IR(KBr) cm$^{-1}$: $\nu_{c=o}$ 1665.
NMR(d$_1$-TFA): 2.0–2.7(2H, m), 3.2–4.7(10H, m), 5.0–5.3(1H, m), 7.12(2H, d, J=9Hz), 7.80(2H, d, J=9Hz).
No. 63
IR(KBr) cm$^{-1}$: $\nu_{c=o}$ 1675.
NMR(d$_1$-TFA): 2.0–2.6(2H, m), 2.9–4.4(13H, m), 4.7–4.9(2H, m), 5.9–6.3 (1H, m), 7.0–7.6(7H, m), 7.80(2H, d, J=9Hz).
No. 64
IR(KBr) cm$^{-1}$: $\nu_{c=o}$ 1665.
NMR(d$_6$-DMSO): 1.8–2.3(2H, m), 2.4–4.5(13H, m), 5.7–6.2(8H, m), 8.5–10.8(4H, m).
No. 65
IR(KBr) cm$^{-1}$: $\nu_{c=o}$ 1685.
NMR(d$_1$-TFA): 2.0–2.5(2H, m), 3.2–4.5(10H, m), 6.0–6.5(1H, m), 7.0–8.0 (8H, m).
No. 66
IR(KBr) cm$^{-1}$: $\nu_{c=o}$ 1665.
NMR(d$_6$-DMSO): 2.0–2.6(2H, m), 3.1–4.5(10, m), 5.9–6.4(3H, m), 6.8–7.3 (5H, m), 7.8(2H, d, J=9Hz).
No. 67
IR(KBr) cm$^{-1}$: $\nu_{c=o}$ 1735, 1685, 1675.
NMR(d$_6$-DMSO+d$_1$-TFA): 1.7–2.3(2H, m), 2.8–4.3(10H, m), 5.8–6.1(1H, m), 6.3–6.6(2H, m), 6.9–8.0(5H, m).
No. 68
IR(KBr) cm$^{-1}$: $\nu_{c=o}$ 1670.
NMR(d$_1$-TFA) δ values: 2.2–2.5(2H, m), 3.2–4.5(10H, m), 6.1–6.4(1H, m), 6.9–8.0(8H, m).
No. 69
IR(KBr) cm$^{-1}$: $\nu_{c=o}$ 1670.
NMR(d$_1$-TFA) δ values: 2.1–2.5(2H, m), 3.2–4.4(10H, m), 6.1–6.4(1H, m), 7.0–8.0(7H, m).
No. 70
IR(KBr) cm$^{-1}$: $\nu_{c=o}$ 1670.
NMR(d$_1$-TFA) δ values: 1.9–2.6(2H, m), 3.08(3H, s), 3.3–4.5(10H, m), 5.9–6.3(1H, m), 7.13(2H, d, J=8Hz), 7.6–8.2(3H, m), 8.4–9.0(2H, m).
No. 71
IR(KBr) cm$^{-1}$: $\nu_{c=o}$ 1670.
NMR(d$_1$-TFA) δ values: 1.9–2.7(2H, m), 3.09(3H, s), 3.3–4.5(10H, m), 5.9–6.4(1H, m), 7.12(2H, d, J=8Hz), 7.5–8.2(4H, m), 8.5–9.0(2H, m).
No. 72
IR(KBr) cm$^{-1}$: $\nu_{c=o}$ 1670.
NMR(d$_1$-TFA) δ values: 2.0–2.6(2H, m), 3.2–4.6(10H, m), 6.0–6.4(1H, m), 6.8–8.0(8H, m).
No. 73
IR(KBr) cm$^{-1}$: $\nu_{c=o}$ 1670.
NMR(d$_1$-TFA) δ values: 2.0–2.7(5H, m), 3.0–4.4(10H, m), 5.9–6.6(1H, m), 6.9–7.6(6H, m), 7.79(2H, d, J=9Hz).
No. 74
IR(KBr) cm$^{-1}$: $\nu_{c=o}$ 1665.
No. 75
IR(KBr) cm$^{-1}$: $\nu_{c=o}$ 1670.
NMR(d$_1$-TFA) δ values: 2.0–2.5(2H, m), 3.2–4.6(13H, m), 6.0–6.4(1H, m), 7.0–8.0(8H, m).
No. 76
IR(KBr) cm$^{-1}$: $\nu_{c=o}$ 1665.
NMR(D$_2$O) δ values: 1.9–2.5(2H, m), 3.08(2H, d, J=8Hz), 3.3–4.5(8H, m), 5.93(1H, t, J=8Hz), 7.05(2H, d, J=9Hz), 7.76(2H, d, J=9Hz), 8.92(2H, s), 9.19(1H, s).
No. 77
IR(KBr) cm$^{-1}$: $\nu_{c=o}$ 1670.
NMR(d$_1$-TFA) δ values: 2.0–2.5(2H, m), 3.3–4.5(10H, m), 6.0–6.4(1H, m), 6.7–8.0(7H, m).
No. 78
IR(KBr) cm$^{-1}$: $\nu_{c=o}$ 1685.
NMR(d$_1$-TFA) δ values: 2.0–2.5(2H, m), 3.0–4.6(13H, m), 5.9–6.5(1H, m), 6.8–8.2(8H, m).
No. 79
IR(KBr) cm$^{-1}$: $\nu_{c=o}$ 1685, 1670.
NMR(d$_1$-TFA) δ values: 1.8–2.3(4H, m), 3.5–4.5(10H, m), 5.8–6.2(1H, m), 7.14(2H, d, J=8.5Hz), 7.83(2H, d, J=8.5Hz), 8.2–8.5(1H, m), 8.8–9.3(3H, m).
No. 80
IR(KBr) cm$^{-1}$: $\nu_{c=o}$ 1670.
NMR(d$_1$-TFA) δ values: 2.0–2.6(2H, m), 3.5–4.5(10H, m), 5.8–6.2(1H, m), 7.17(2H, d, J=9Hz), 7.83(2H, d, J=9Hz), 8.33(2H, d, J=7Hz), 8.95(2H, d, J=7Hz).
No. 81
IR(KBr) cm$^{-1}$: $\nu_{c=o}$ 1675.
NMR(d$_1$-TFA) δ values: 1.9–2.5(2H, m), 3.4–4.5(10H, m), 5.7–6.6(1H, m), 6.9–9.0(6H, m).
No. 82
IR(KBr) cm$^{-1}$: $\nu_{c=o}$ 1665.
NMR(d$_1$-TFA) δ values: 0.8–2.0(9H, m), 2.1–2.5(2H, m), 2.9(2H, d, J=8Hz), 3.7–4.6(8H, m), 4.7–5.2(1H, m), 7.16(2H, d, J=9Hz), 7.83(2H, d, J=9Hz).
No. 83
IR(KBr) cm$^{-1}$: $\nu_{c=o}$ 1665.
NMR(d$_1$-TFA) δ values: 0.3–1.4(5H, m), 2.1–2.5(2H, m), 2.9–3.2(2H, m), 3.7–4.5(9H, m), 7.14(2H, d, J=9Hz), 7.81(2H, d, J=9Hz).
No. 84
IR(KBr) cm$^{-1}$: $\nu_{c=o}$ 1665.
NMR(d$_1$-TFA) δ values: 2.1–2.5(2H, m), 3.3–4.5(10H, m), 6.2–6.6(1H, m), 6.9–7.4(3H, m), 7.5–8.3(8H, m).
No. 85
IR(KBr) cm$^{-1}$: $\nu_{c=o}$ 1665.
NMR(d$_1$-TFA) δ values: 2.0–2.5(2H, m), 3.1–4.5(10H, m), 6.8–7.2(3H, m), 7.3–8.5(9H, m).
No. 86
IR(KBr) cm$^{-1}$: $\nu_{c=o}$ 1665.
NMR(d$_1$-TFA) δ values: 2.0–2.6(2H, m), 3.3–4.4(10H, m), 6.2–6.7(1H, m), 6.9–8.2(9H, m).
No. 87
IR(KBr) cm$^{-1}$: $\nu_{c=o}$ 1670.
NMR(d$_1$-TFA) δ values: 1.9–2.5(2H, m), 3.4–4.7(11H, m), 7.12(2H, d, J=9Hz), 7.43(5H, s), 7.80(2H, d, J=9Hz).

Example 88

Ethyl 3-[4-[3-(4-amidinophenoxy)propyl]-2,3-dioxopiperazin-1yl]-3-(pyridin-3-yl)propionate hydrochloride

In 2 ml of ethyl acetate was dissolved 0.45 g of ethyl 3-[4-[3-(4-tert-butoxycarbonylamidinophenoxy)-propyl]-2,3-dioxopiperazin-1-yl]-3-(pyridin-3-yl)-propionate, followed by adding thereto 4 ml of a 2.4N solution of hydrochloric acid in dioxane, and the resulting mixture was stirred at room temperature for 12 hours. After completion of the reaction, the solvent was distilled off under reduced pressure and the resulting residue was purified by a reversed phase column chromatography (eluent: a 15% aqueous acetonitrile solution) to obtain 0.20 g of ethyl 3-[4-[3-(4-amidinophenoxy) propyl]-2,3-dioxopiperazin-1-yl]-3-(pyridin-3-yl) propionate hydrochloride as a white solid.

IR (KBr) cm$^{-1}$: $\nu_{C=O}$ 1735, 1670.

NMR (D$_2$O) δ values: 1.29 (3H, t, J=7 Hz), 2.0–2.5 (2H, m), 3.2–4.5 (12H, m), 5.9–6.3 (1H, m), 7.12 (2H, d, J=9 Hz), 7.6–8.3 (4H, m), 8.6–8.8 (2H, m).

Example 89

Diphenylmethyl 3-[4-[2-(4-tert-butoxycarbonyl-amidinobenzoyl) aminoethyl]-2,3-dioxopiperazin-1-yl]-3-(pyridin-3-yl)propionate To a mixture of 0.19 g of 4-tert-butoxycarbonylamidinobenzoic acid, 0.09 g of N-hydroxysuccinimide and 1 ml of N,N-dimethylformamide was added 0.17 g of N,N'-dicyclohexylcarbodiimide, and the resulting mixture was stirred at room temperature for 3 hours. To the reaction mixture was added a solution of 0.2 g of diphenylmethyl 3-[4-(2-aminoethyl)-2,3-dioxopiperazin-1yl]-3-(pyridin-3-yl)propionate in 2 ml of methylene chloride. The resulting mixture was stirred at room temperature for 6 hours, followed by adding thereto 30 ml of ethyl acetate and 20 ml of water. The organic layer was separated, washed with water and then a saturated aqueous sodium chloride solution, and then dried over anhydrous magnesium sulfate. The solvent was distilled off under reduced pressure and the resulting residue was purified by a silica gel column chromatography (eluent; chloroform: methanol=10:1) to obtain 0.16 g of diphenylmethyl 3-[4-[2-(4-tert-butoxycarbonylamidinobenzoyl) aminoethyl]-2,3-dioxopiperazin-1-yl]-3-(pyridin-3-yl) propionate as a light-yellow oil.

IR (KBr) cm$^{-1}$: $\nu_{C=O}$ 1735, 1670.

NMR (CDCl$_3$) δ values: 1.56 (9H, s), 3.1–3.9 (10H, m), 5.6–6.0 (1H, m), 6.79 (1H, s), 7.0–8.8 (21H, m).

Examples 90 to 96

The compounds listed in Table 12 were obtained in the same manner as in Example 89.

TABLE 12

BocNH-C(=NH)-C$_6$H$_4$-CONH-Y-N(dioxopiperazine)N-A-COOR$^{2a}$

| Example No. | Y | A | R$^{2a}$ |
|---|---|---|---|
| 90 | +CH$_2$+$_3$ | —CHCH$_2$— (pyridin-3-yl) | DPM |
| 91 | +CH$_2$+$_2$ | —CH$_2$CH$_2$— | DPM |
| 92 | +CH$_2$+$_3$ | —CH$_2$CH$_2$— | DPM |
| 93 | +CH$_2$+$_2$ | —CH$_2$CH— (2,3-dihydrobenzofuran) | DPM |
| 94 | +CH$_2$+$_3$ | —CH$_2$CH— (2,3-dihydrobenzofuran) | DPM |
| 95 | +CH$_2$+$_2$ | —CH$_2$— | t-Bu |
| 96 | +CH$_2$+$_3$ | —CH$_2$— | DPM |

Physical properties of the compounds listed in Table 12 are shown below.
No. 90
IR KBr cm$^{-1}$: $\nu_{C=O}$ 1735, 1670.
NMR(d$_6$-DMSO) δ values: 1.3–2.1(11H, m), 3.0–4.2(10H, m), 5.8–6.2(1H, m), 6.82(1H, s), 7.2–9.3(21H, m).
No. 91
IR(KBr) cm$^{-1}$: $\nu_{C=O}$ 1735, 1670.
NMR(CDCl$_3$) δ values: 1.54(9H, s), 2.6–3.0(2H, m), 3.2–3.8(10H, m), 6.85(1H, s), 7.30(10H, s), 7.6–8.4(7H, m).
No. 92
IR(KBr) cm$^{-1}$: $\nu_{C=O}$ 1735, 1665.
NMR(d$_6$-DMSO) δ values: 1.4–2.1(11H, m), 2.6–4.2(12H, m), 6.8–7.0(1H, m), 7.2–8.4(17H, m).
No. 93
IR(KBr) cm$^{-1}$: $\nu_{C=O}$ 1735, 1670.
NMR(CDCl$_3$) δ values: 1.55(9H, s), 2.7–4.2(13H, m), 5.7–6.1(2H, m), 6.4–8.3(20H, m).
No. 94
IR(KBr) cm$^{-1}$: $\nu_{C=O}$ 1735, 1670.
NMR(CDCl$_3$) δ values: 1.5–2.1(11H, m), 2.6–3.6(13H, m), 5.8–5.9(2H, m), 6.5–8.7(21H, m).
No. 95
IR(KBr) cm$^{-1}$: $\nu_{C=O}$ 1735, 1670.
NMR(CDCl$_3$) δ values: 1.44(9H,s), 1.55(9H, s), 3.5–3.9(8H, m), 4.09(2H, s), 7.7–8.5(7H, m).
No. 96
IR(KBr) cm$^{-1}$: $\nu_{C=O}$ 1760, 1675.
NMR(CDCl$_3$) δ values: 1.4–2.1(11H, m), 3.2–3.8(8H, m), 4.33(2H, s), 6.90(1H, s), 7.3–8.1(17H, m).

Example 97

3-[4-[2-(4-Amidinobenzoyl)aminoethyl]-2,3-dioxopiperazin-1yl]-3-(pyridin-3-yl)propionic acid To a mixture of 0.1 g of diphenylmethyl 3-[4-[2-(4-tert-butoxycarbonylamidinobenzoyl)aminoethyl]-2,3-dioxopiperazin-1yl]-3-(pyridin-3-yl)propionate and 1 ml of anisole was added 2 ml of trifluoroacetic acid, and the resulting mixture was stirred at room temperature for 3 hours. Then, the solvent was distilled off under reduced pressure and 2 ml of ethyl acetate, 1 ml of water and 1 ml of acetonitrile were added to the residue. To the resulting mixture was added 0.023 g of sodium hydrogencarbonate, followed by stirring at room temperature for 10 minutes. Thereafter, the aqueous layer was separated and then concentrated to a volume of about 0.5 ml under reduced pressure. The resulting concentrate was purified by a reversed phase column chromatography (eluent: a 10% aqueous acetonitrile solution) to obtain 0.02 g of 3-[4-[2-(4-amidinobenzoyl) aminoethyl]-2,3-dioxopiperazin-1-yl]-3-(pyridin-3-yl) propionic acid as colorless crystals.

IR (KBr) cm$^{-1}$: $\nu_{C=O}$ 1665.

NMR (d$_1$-TFA) δ values: 3.5–4.4 (10H, m), 5.7–6.2 (1H m), 7.9–8.6 (5H, m), 8.8–9.1 (2H, m), 9.23 (1H s).

Examples 98 to 104

The compounds listed in Table 13 were obtained in the same manner as in Example 97.

TABLE 13

[Structure: HN=C(NH₂)-C₆H₄-CONH-Y-N(piperazine-2,3-dione)-A-COOH]

| Example No. | Y | A | Salt |
|---|---|---|---|
| 98 | ─(CH₂)₃─ | ─CHCH₂─ (pyridyl) | — |
| 99 | ─(CH₂)₂─ | ─CH₂CH₂─ | HCl* |
| 100 | ─(CH₂)₃─ | ─CH₂CH₂─ | — |
| 101 | ─(CH₂)₂─ | ─CH₂CH─(CH₂-benzodioxole) | — |
| 102 | ─(CH₂)₃─ | ─CH₂CH─(CH₂-benzodioxole) | — |
| 103 | ─(CH₂)₂─ | ─CH₂─ | HCl* |
| 104 | ─(CH₂)₃─ | ─CH₂─ | HCl* |

*Each hydrochloride was obtained by treating a product obtained by purification by a reversed phase column chromatography, with 6N hydrochloric acid.

Physical properties of the compounds listed in Table 13 are shown below.

No. 98
IR(KBr) cm$^{-1}$: $v_{C=O}$ 1670.
NMR(d$_1$-TFA) δ values: 1.9–2.5(2H, m), 3.4–4.4(10H, m), 5.7–6.2(1H, m), 7.8–9.4(8H, m).

No. 99
IR(KBr) cm$^{-1}$: $v_{C=O}$ 1705, 1665.
NMR(d$_6$-DMSO) δ values: 2.2–2.7(2H, m), 3.0–3.8(10H, m), 7.7–8.1(4H, m), 8.4–9.8(6H, m).

No. 100
IR(KBr) cm$^{-1}$: $v_{C=O}$ 1700, 1675.
NMR(d$_1$-TFA) δ values: 1.9–2.4(2H, m), 3.00(2H, t, J=6Hz), 3.5–4.3(10H, m), 7.9–8.3(4H, m).

No. 101
IR(KBr) cm$^{-1}$: $v_{C=O}$ 1735, 1670.
NMR(d$_1$-TFA) δ values: 2.7–4.3(13H, m), 5.7–6.1(2H, m), 6.5–6.9(3H, m), 7.7–8.1(4H, m).

No. 102
IR(KBr) cm$^{-1}$: $v_{C=O}$ 1665.
NMR(d$_1$-TFA) δ values: 2.0–2.4(2H, m), 3.0–4.8(13H, m), 5.98(2H, s), 6.83(3H, s), 7.96(2H, d, J=8.5Hz), 8.12(2H, d, J=8.5Hz).

No. 103
IR(KBr) cm$^{-1}$: $v_{C=O}$ 1775, 1670.
NMR(d$_1$-TFA) δ values: 3.7–4.3(8H, m), 4.54(2H, s), 7.9–8.2(4H, m).

No. 104
IR(KBr) cm$^{-1}$: $v_{C=O}$ 1685, 1655.
NMR(d$_6$-DMSO) δ values: 1.6–2.2(2H, m), 3.3–4.2(10H, m), 7.8–9.5(10H, m).

Example 105

[4-[3-(4-Amidinobenzenesulfonylamino)propyl]-2,3-dioxopiperazin-1-yl]acetic acid (1) Hydrogen sulfide gas was introduced into a mixture of 0.48 g of diphenylmethyl [4-[3-(4-cyanobenzenesulfonylamino) propyl]-2,3-dioxopiperazin-1-yl]-acetate, 2.4 ml of triethylamine and 4.8 ml of pyridine at room temperature until the mixture was saturated therewith. After stirring at the same temperature for 5 hours, the reaction mixture was added to a mixed solvent of 30 ml of ethyl acetate and 30 ml of water, and the pH was adjusted to 4 with 6N hydrochloric acid. The organic layer was separated and the aqueous layer was re-extracted with 10 ml of ethyl acetate. The combined organic layer was washed with water and then a saturated aqueous sodium chloride solution, dried over anhydrous magnesium sulfate, and then distilled under reduced pressure to remove the solvent. The resulting residue was purified by a silica gel column chromatography (eluent; chloroform: methanol=20:1) to obtain 0.40 g of diphenylmethyl [4-[3-(4-thiocarbamoylbenzenesulfonylamino) propyl]-2,3-dioxopiperazin-1-yl]acetate as yellow crystals.

IR (KBr) cm$^{-1}$: $v_{C=O}$ 1745, 1675.

NMR (d$_6$-DMSO) δ values: 1.4–2.1 (2H, m), 2.4–3.0 (2H, m), 3.1–3.8 (6H, m), 4.40 (2H, s), 6.86 (1H, s), 7.1–8.5 (15H, m), 9.5–10.3 (2H, m).

(2) A mixture of 0.30 g of diphenylmethyl [4-[3-(4-thiocarbamoylbenzenesulfonylamino)propyl]-2,3-dioxopiperazin-1yl]acetate, 0.6 ml of methyl iodide and 3 ml of acetone was refluxed for 30 minutes and then distilled under reduced pressure to remove the solvent. To the residue were added 3 ml of methanol and 0.08 g of ammonium acetate, and the resulting mixture was heated under reflux for 3 hours. After the solvent was distilled off under reduced pressure, 1.2 ml of trifluoroacetic acid and 0.6 ml of anisole were added to the residue and the resulting mixture was allowed to stand overnight at room temperature. The reaction mixture was concentrated under reduced pressure, after which 5 ml of ethyl acetate and 5 ml of water were added to the residue and the pH was adjusted to 3 with a saturated aqueous sodium hydrogencarbonate solution. The aqueous layer was separated and then concentrated to a volume of about 5 ml. The resulting concentrate was purified by a reversed phase column chromatography (eluent: a 25% aqueous acetonitrile solution) to obtain 0.13 g of [4-[3-(4-amidinobenzenesulfonylamino)propyl]-2,3-dioxopiperazin-1-yl]acetic acid as colorless crystals.

IR (KBr) cm$^{-1}$: $v_{C=O}$ 1685, 1655.

NMR (D$_2$O) δ values: 1.6–2.1 (2H, m), 3.02 (2H, t, J=6 Hz), 3.3–3.9 (6H, m), 4.02 (2H, S), 8.04 (4H, s).

Example 106 tert-Butyl [4-[4-(4-benzyloxycarbonylamidinophenylamino) -4-oxobutyl]-2,3-dioxopiperazin-1-yl] acetate To 9 ml of a tetrahydrofuran solution containing 0.18 g of 4-(4-tert-butoxycarbonylmethyl-2,3-dioxopiperazin- 1-yl) butyric acid were added 0.16 ml of triethylamine and then 0.15 ml of chlorotrimethylsilane, and the resulting mixture was stirred at room temperature for 30 minutes. The reaction mixture was cooled to −10°C., after which 0.10 ml of oxalyl chloride was added thereto and the resulting mixture was stirred at the same temperature for 30 minutes. Then, 0.15 ml of 4-benzyloxyamidinoaniline and 0.80 ml of triethylamine were added thereto, followed by stirring at the same temperature for 10 minutes and then at 0° C. for 1 hour. After completion of the reaction, the insoluble materials were filtered off and the filtrate was concentrated under reduced pressure. The concentrate was purified by a silica gel column chromatography (eluent; chloroform: methanol=20:1) to obtain 0.21 g of tert-butyl [4-[4-(4-benzyloxycarbonylamidinophenylamino) -4-oxobutyl]-2,3-dioxopiperazin-1-yl]acetate as a yellow oil.

IR (KBr) cm$^{-1}$: $v_{C=O}$ 1735, 1685.

NMR (CDCl$_3$) δ values: 1.44 (9H, s), 1.8–2.7 (4H, m), 2.8–3.8 (6H, m), 4.05 (2H, s), 5.19 (2H, s), 6.8–7.1 (1H, m), 7.2–7.9 (11H, m).

Example 107

[4-[4-(4-Amidinophenylamino)-4-oxobutyl]-2,3-dioxopiperazin-1yl]acetic acid

To a solution of 0.28 g of tert-butyl [4-[4-(4-benzyloxycarbonylamidinophenylamino)-4-oxobutyl]-2,3-dioxopiperazin-1-yl]acetate in 2.8 ml of methylene chloride was added 1.4 ml of trifluoroacetic acid, and the resulting mixture was stirred at room temperature for 12 hours and then distilled under reduced pressure to remove the solvent. To the resulting residue were added 0.08 g of 5% palladium-carbon and 5.6 ml of N,N-dimethylformamide, followed by hydrogenation at ordinary temperature and atmospheric pressure for 3 hours. After completion of the reaction, the catalyst was filtered off and the filtrate was concentrated under reduced pressure. To the resulting concentrate were added 5 ml of water and 0.042 g of sodium hydrogencarbonate to obtain a homogeneous solution. This solution was purified by a reversed phase column chromatography (eluent: a 10% aqueous acetonitrile solution) to obtain 0.08 g of [4-[4-(4-amidinophenylamino)-4-oxobutyl]-2,3-dioxopiperazin-1yl]acetic acid as colorless crystals.

IR (KBr) cm$^{-1}$: $v_{C=O}$ 1675.

NMR (d$_1$-TFA) δ values: 1.9–3.1 (4H, m), 3.3–4.6 (8H, m), 7.5–8.8 (4H, m).

Example 108

(–)-3-[4-[3-(4-Amidinophenoxy)propyl]-2,3-dioxopiperazin-1yl]-3-(pyridin-3-yl)propionic acid trihydrate In 20 ml of water was suspended 3.1 g of the (–)-3-[4-[3-(4-amidinophenoxy)propyl]-2,3-dioxopiperazin-1-yl]-3-(pyridin-3-yl)propionic acid obtained in Example 57, and the suspension was heated to obtain a homogeneous solution. This solution was allowed to stand overnight at room temperature, after which the crystals precipitated were collected by filtration, washed with 3 ml of water, and then dried at room temperature to obtain 2.58 g of (–)-3-[4-[3-(4-amidinophenoxy) propyl]-2,3-dioxopiperazin-1-yl]-3-(pyridin-3-yl) propionic acid trihydrate as colorless crystals having a melting point of 238°–240° C. (decomp.).

IR (KBr) cm$^{-1}$: $v_{C=O}$ 1655.

[α]$_d$ -81.5 (C=1.4, H$_2$O)

INDUSTRIAL APPLICABILITY

The compound of the present invention has inhibitory effect on platelet aggregation and hence is useful as a prophylactic and therapeutic agent for diseases associated with platelet aggregation.

We claim:

1. A 2,3-diketopiperazine compound represented by the formula, or its pharmaceutically acceptable salt:

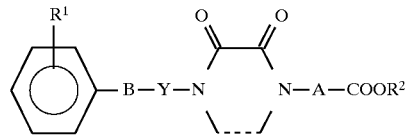

wherein R$^1$ represents a protected or unprotected amidino group; R$^2$ represents a hydrogen atom or a carboxyl-protecting group; A represents a lower alkylene group, which may be substituted by at least one member (A substituents) selected from the group consisting of a lower alkyl group, a lower alkoxy group, a cycloalkyl group, a phenyl group, a tolyl group, a naphthyl group, a benzyl group, a benzhydryl group, a trityl group, a phenethyl group, a benzodioxolyl group, a pyridyl group, a carbamoyl group, a protected or unprotected amino group, a protected or unprotected hydroxyl group, and a protected or unprotected carboxyl group, and wherein said A substituents may be further substituted by at least one member selected from the group consisting of a halogen atom, a lower alkyl group, a lower alkoxy group, a protected or unprotected hydroxyl group, a benzyl group, a benzhydryl group, a trityl group and a phenethyl group; B represents —O—, —CONH—, —NHCO—or —SO$_2$NH—; Y represents a lower alkylene group which may be substituted by at least one member (Y substituents) selected from the group consisting of a lower alkyl group, a lower alkoxy group, a cycloalkyl group, a phenyl group, a tolyl group, a naphthyl group, a benzyl group, a benzhydryl group, a trityl group, a phenethyl group, and a protected or unprotected hydroxyl group; and wherein said Y substituents may be further substituted by at least one member selected from the group consisting of a halogen atom, a lower alkyl group, a lower alkoxy group, a protected or unprotected hydroxyl group, a benzyl group, a benzhydryl group, a trityl group and a phenethyl group; and the broken line represents a single bond or a double bond.

2. The 2,3-diketopiperazine compound or its pharmaceutically acceptable salt according to claim 1, wherein B represents —O—.

3. The 2,3-diketopiperazine compound or its pharmaceutically acceptable salt according to claim 2, wherein Y represents an unsubstituted lower alkylene group.

4. The 2,3-diketopiperazine compound or its pharmaceutically acceptable salt according to claim 3, wherein R$^1$ represents an amidino group.

5. The 2,3-diketopiperazine compound or its pharmaceutically acceptable salt according to claim 4, wherein the broken line represents a single bond.

6. The 2,3-diketopiperazine compound or its pharmaceutically acceptable salt according to claim 5, wherein A represents a lower alkylene group substituted by A substituents selected from the group consisting of a phenyl group, a tolyl group, a naphthyl group a benzodioxolyl group and a pyridyl group, and wherein said A substituents may be further substituted by at least one member selected from the group consisting of a halogen atom, a lower alkyl group, a lower alkoxy group, a protected or unprotected hydroxyl group, a benzyl group, a benzhydryl group, a trityl group and a phenethyl group.

7. The 2,3-diketopiperazine compound or its pharmaceutically acceptable salt according to claim 6, wherein A represents a lower alkylene group substituted by a phenyl group which may be substituted by a halogen atom, a lower alkoxy group or A is substituted by a benzodeopolyl group.

8. The 2,3-diketopiperazine compound or its pharmaceutically acceptable salt according to claim 6, wherein A represents a lower alkylene group substituted by a pyridyl group.

9. The 2,3-diketopiperazine compound or its pharmaceutically acceptable salt according to claim 1, wherein B represents —CONH—.

10. The 2,3-diketopiperazine compound or its pharmaceutically acceptable salt according to claim 9, wherein Y represents an unsubstituted lower alkylene group.

11. The 2,3-diketopiperazine compound or its pharmaceutically acceptable salt according to claim 10, wherein $R^1$ represents an amidino group.

12. The 2,3-diketopiperazine compound or its pharmaceutically acceptable salt according to claim 11, wherein the broken line represents a single bond.

13. The 2,3-diketopiperazine compound or its pharmaceutically acceptable salt according to claim 12, wherein A represents a lower alkylene group which may be substituted by A substituents selected from the group consisting of a phenyl group, a tolyl group, a naphthyl group a benzodioxolyl group and a pyridyl group, and wherein said A substituents may be further substituted by at least one member selected from the group consisting of a halogen atom, a lower alkyl group, a lower alkoxy group, a protected or unprotected hydroxyl group, a benzyl group, a benzhydryl group, a trityl group and a phenethyl group.

14. The 2,3-diketopiperazine compound or its pharmaceutically acceptable salt according to claim 1, wherein B represents —NHCO—.

15. The 2,3-diketopiperazine compound or its pharmaceutically acceptable salt according to claim 14, wherein Y represents an unsubstituted lower alkylene group.

16. The 2,3-diketopiperazine compound or its pharmaceutically acceptable salt according to claim 15, wherein $R^1$ represents an amidino group.

17. The 2,3-diketopiperazine compound or its pharmaceutically acceptable salt according to claim 16, wherein the broken line represents a single bond.

18. The 2,3-diketopiperazine compound or its pharmaceutically acceptable salt according to claim 1, wherein B represents —SO$_2$NH—.

19. The 2,3-diketopiperazine compound or its pharmaceutically acceptable salt according to claim 18, wherein Y represents an unsubstituted lower alkylene group.

20. The 2,3-diketopiperazine compound or its pharmaceutically acceptable salt according to claim 19, wherein $R^1$ represents an amidino group.

21. The 2,3-diketopiperazine compound or its pharmaceutically acceptable salt according to claim 20, wherein the broken line represents a single bond.

22. 3-[4-[3-(4-Amidinophenoxy)propyl]-2,3-dioxopiperazin-1-yl]- 3-(pyridin-3-yl)propionic acid or its optical isomer, or a pharmaceutically acceptable salt of either of them.

23. 3-[4-[3-(4-Amidinophenoxy)propyl]-2,3-dioxopiperazin-1-yl]-3-phenylpropionic acid or its optical isomer, or a pharmaceutically acceptable salt of either of them.

24. 3-[4-[3-(4-Amidinophenoxy)propyl]-2,3-dioxopiperazin-1-yl]-3-(2-methoxyphenyl) propionic acid or its optical isomer, or a pharmaceutically acceptable salt of either of them.

25. 3-[4-[3-(4-Amidinophenoxy)propyl]-2,3-dioxopiperazin-1-yl]-3-(3-methoxyphenyl) propionic acid or its optical isomer, or a pharmaceutically acceptable salt of either of them.

26. 3-[4-[3-(4-Amidinophenoxy)propyl]-2,3-dioxopiperazin-1-yl]-3-(4-methoxyphenyl) propionic acid or its optical isomer, or a pharmaceutically acceptable salt of either of them.

27. 3-[4-[3-(4-Amidinophenoxy)propyl]-2,3-dioxopiperazin-1-yl]-3-(2,3-methylenedioxyphenyl)-propionic acid or its optical isomer, or a pharmaceutically acceptable salt of either of them.

28. 3-[4-[3-(4-Amidinophenoxy)propyl]-2,3-dioxopiperazin-1-yl]-3-(thiophen-3-yl) propionic acid or its optical isomer, or a pharmaceutically acceptable salt of either of them.

29. 3-[4-[3-(4-Amidinophenoxy)propyl]-2,3-dioxopiperazin-1-yl]-3-(2,4-difluorophenyl) propionic acid or its optical isomer, or a pharmaceutically acceptable salt of either of them.

30. A pharmaceutical composition comprising a pharmaceutically effective amount of a 2,3-diketo-piperazine compound or a pharmaceutically acceptable salt thereof as claimed in any one of claims 1 to 29 and a pharmaceutically acceptable adjuvant.

31. A method of inhibiting platelet aggregation comprising administering to a subject in need thereof a 2,3-diketopiperazine compound represented by the formula, or its pharmaceutically acceptable salt:

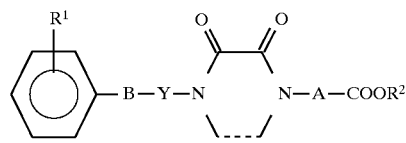

wherein $R^1$ represents an amidino group which may be substituted by an acyl group; $R^2$ represents a hydrogen atom, a lower alkyl or an ar-lower alkyl group; A represents a lower alkylene group which may be substituted by at least one member (A substituents) selected from the group consisting of a lower alkyl group, a lower alkoxy group, a cycloalkyl group, a phenyl group, a tolyl group, a naphthyl group, a benzyl group, a benzhydryl group, a trityl group, a phenethyl group, a benzodioxolyl group a pyridyl group, a carbamoyl group, an amino group, a hydroxyl group, and a carboxyl group, and wherein said A substituents may be further substituted by at least one member selected from the group consisting of a halogen atom, a lower alkyl group, a lower alkoxy group, a hydroxyl group, a benzyl group, a benzhydryl group, a trityl group, and a phenethyl group; B represents —O—, —CONH—, —NHCO— or —SO$_2$NH—; Y represents a lower alkylene group which may be substituted by at least one member (Y substituents) selected from the group consisting of a lower alkyl group, a lower alkoxy group, a cycloalkyl group, a phenyl group, a tolyl group, a naphthyl group, a benzyl group, a benzhydryl group, a trityl group, a phenethyl group, and a hydroxyl group; and wherein said Y substituents may be further substituted by at least one member selected from the group consisting of a halogen atom, a lower alkyl group, a lower alkoxy group, a hydroxyl group, a benzyl group, a benzhydryl group, a trityl group and a phenethyl group; and the broken line represents a single bond or a double bond.

* * * * *